US006485905B2

(12) United States Patent
Hefti

(10) Patent No.: US 6,485,905 B2
(45) Date of Patent: *Nov. 26, 2002

(54) BIO-ASSAY DEVICE

(75) Inventor: John Hefti, San Francisco, CA (US)

(73) Assignee: Signature BioScience, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 26 days.

(21) Appl. No.: 09/365,978

(22) Filed: Aug. 2, 1999

(65) Prior Publication Data

US 2002/0137032 A1 Sep. 26, 2002

Related U.S. Application Data

(63) Continuation-in-part of application No. 09/243,194, filed on Feb. 1, 1999, now Pat. No. 6,368,794.
(60) Provisional application No. 60/073,445, filed on Feb. 2, 1998, and provisional application No. 60/134,740, filed on May 18, 1999.

(51) Int. Cl.[7] .................. G01N 33/543; G01N 33/68
(52) U.S. Cl. .................. 435/6; 422/82.01; 435/4; 435/7.1; 435/7.2; 435/287.1; 435/287.2; 436/149; 436/150; 436/151; 436/517; 436/518; 436/524; 436/805; 436/806
(58) Field of Search .............. 435/4, 6, 7.1, 7.92, 435/7.2, 287.1, 287.2; 436/517, 518, 149, 150, 151, 805, 806, 524; 422/82.01

(56) References Cited

U.S. PATENT DOCUMENTS 4,822,566 A * 4/1989 Newman ............... 422/68
5,025,222 A 6/1991 Scott (List continued on next page.)

FOREIGN PATENT DOCUMENTS

| EP | 0519250 A2 * | 12/1992 | ......... G01N/33/543 |
| WO | WO 93 08464 | 4/1993 | |
| WO | WO 97/41425 | 4/1996 | |

(List continued on next page.)

OTHER PUBLICATIONS

Ferguson et al. (1996). A fiber–optic DNA biosensor microarray for the analysis of gene expression. Nature Biotech. 14:1681–1684.*

Eggers et al. (1994). A microchip for quantitative detection of molecules utilizing luminescent and radioisotope reporter groups. BioTechniques. 17(3):516–523.*

Stimpson et al. (1995). Real–time detection of DNA hybridization and melting on oligonucleotide arrays by using optical wave guides. PNAS USA. 92:6379–6383.*

(List continued on next page.)

Primary Examiner—Christopher L. Chin
(74) Attorney, Agent, or Firm—Clifford Perry; Richard Neeley

(57) ABSTRACT

A bio-assay test system includes a test fixture, a measurement system, and a computer. The test fixture includes a bio-assay device having a signal path and a retaining structure configured to place a sample containing molecular structures in electromagnetic communication with the signal path. The measurement system is configured to transmit test signals to and to receive test signals from the signal path at one or more predefined frequencies. The computer is configured to control the transmission and reception of the test signals to and from the measurement system.

7 Claims, 23 Drawing Sheets

U.S. PATENT DOCUMENTS

| | | | |
|---|---|---|---|
| 5,082,630 A | * 1/1992 | Partin et al. | 422/83 |
| 5,156,810 A | * 10/1992 | Ribi | 422/82.01 |
| 5,164,319 A | * 11/1992 | Hafeman et al. | 435/291 |
| 5,327,225 A | * 7/1994 | Bender et al. | 356/445 |
| 5,340,715 A | * 8/1994 | Slovacek et al. | 435/6 |
| 5,341,215 A | * 8/1994 | Seher | 356/445 |
| 5,363,052 A | 11/1994 | McKee | |
| 5,466,348 A | 11/1995 | Holm-Kennedy | |
| 5,478,755 A | * 12/1995 | Attridge et al. | 436/518 |
| 5,485,277 A | * 1/1996 | Foster | 356/445 |
| 5,512,492 A | * 4/1996 | Herron et al. | 436/518 |
| 5,525,466 A | * 6/1996 | Slovacek et al. | 435/6 |
| 5,532,128 A | * 7/1996 | Eggers et al. | 435/16 |
| 5,532,493 A | * 7/1996 | Hale et al. | 250/458.1 |
| 5,563,939 A | 10/1996 | La Porta et al. | 379/220 |
| 5,599,668 A | * 2/1997 | Stimpson et al. | 435/6 |
| 5,629,213 A | * 5/1997 | Kornguth et al. | 436/518 |
| 5,647,030 A | * 7/1997 | Jorgenson et al. | 385/12 |
| 5,653,939 A | * 8/1997 | Hollis et al. | 422/50 |
| 5,656,428 A | 8/1997 | McAllister et al. | |
| 5,738,992 A | * 4/1998 | Cook et al. | 435/6 |
| 5,822,073 A | * 10/1998 | Yee et al. | 356/445 |
| 5,827,482 A | * 10/1998 | Shieh et al. | 422/82.02 |
| 5,832,165 A | * 11/1998 | Reichert et al. | 385/130 |
| 5,835,645 A | * 11/1998 | Jorgenson et al. | 385/12 |
| 5,841,914 A | 11/1998 | Shieh et al. | |
| 5,843,651 A | * 12/1998 | Stimpson et al. | 435/6 |
| 5,846,708 A | * 12/1998 | Hollis et al. | 435/6 |
| 5,846,842 A | * 12/1998 | Herron et al. | 436/518 |
| 5,846,843 A | * 12/1998 | Simon | 436/527 |
| 5,858,666 A | * 1/1999 | Weiss | 435/6 |
| 5,858,799 A | * 1/1999 | Yee et al. | 436/164 |
| 5,869,261 A | * 2/1999 | Tosa | 435/7.1 |
| 5,919,712 A | * 7/1999 | Herron et al. | 136/518 |
| 5,955,729 A | * 9/1999 | Nelson et al. | 250/282 |
| 5,961,924 A | * 10/1999 | Reichert et al. | 422/82.11 |
| 5,965,456 A | * 10/1999 | Malmqvist et al. | 436/514 |
| 5,966,017 A | 10/1999 | Scott et al. | |
| 5,991,048 A | * 11/1999 | Karlson et al. | 356/455 |
| 6,048,692 A | 4/2000 | Maracas et al. | |
| 6,057,167 A | 5/2000 | Shieh et al. | |
| 6,060,023 A | 5/2000 | Maracas | |
| 6,203,981 B1 | 3/2001 | Ackley et al. | |
| 6,210,910 B1 | * 4/2001 | Walt et al. | 435/7.32 |

FOREIGN PATENT DOCUMENTS

| | | |
|---|---|---|
| WO | WO 96/36871 | 11/1996 |
| WO | WO 98 09168 | 3/1998 |
| WO | WO 98 31839 | 7/1998 |

OTHER PUBLICATIONS

Frutos et al. (1998). SPR of ultrathin organic films. Anal. Chem. News & Features. Jul. 1, 1998, pp. 449A–455A.*

Hanken et al. (1997). Synthesis, spectroscopic characterization, and electro–optical properties of nancentrosymetric azabenzene/zirconium phhosphate multilayer films. Anal. Chem. 69(2):240–248.*

Hollis et al. (1980). A swept–frequency magnitude method for the dielectric characterization of chemical and biological system. IEEE Trans. Microw. Theory and Techniques. MTT–28(7):791–801.*

Hollis et al., *A Swept Frequency Magnitude Method for the Dielectric Characterization of Chemical and Biological Systems*, IEEE Transactions on Microwave Theory and Techniques, vol. MTT–28, No. 7, Jul. 1980, pp. 791–801.

Amo et al., "Dielectric Measurements of Lysozyme and Tri–N–Acetyl–D–Glucosamine Association at Radio and Microwave Frequencies", Biosensors & Bioelectronics, 12(9–10):953–958 (1997).

Hianik, "Biosensors Based on Solid Supported Lipid Bilayers and their Physical Properties", Nato Asi Ser., Ser. 2 (1997), 38 (Biosensors for Direct Monitoring of Environmental Pollutanta in Field), 317–333.

Smith et al., "Dielectric Relaxation Spectroscopy and Some Applications in the Pharmaceutical Sciences", Journal of Pharmaceutical Sciences, 84(9):1029–1044 (1995).

* cited by examiner

BIO-ASSAY DEVICE

CROSS-REFERENCES TO RELATED APPLICATIONS

This application is a continuation-in-part application of U.S. application Ser. No. 09/243,194, entitled "Method and Apparatus for Detecting Molecular Binding Events," filed Feb. 1, 1999, now U.S. Pat. No. 6,768,795 which claims the benefit of U.S. Provisional Application No. 60/073,445, entitled "Detection of Molecular Binding Events on a Conductive Surface," filed Feb. 2, 1998.

Further, the following applications are herein incorporated by reference in their entirety for all purposes:

"A Sensitive Detection of Dispersions in Aqueous-based, Surface-bound Macromolecular Structures Using Microwave Spectroscopy," serial No. 60/134,740, filed May 18, 1999;

"Methods of Nucleic Acid Analysis," Ser. No. 09/365,581 filed concurrently herewith; and Methods for Analyzing Protein Binding Events," Ser. No. 09/365,580 also filed currently herewith.

BACKGROUND

Virtually every area of the biomedical sciences is in need of a system to assay chemical and biochemical reactions and determine the presence and quantity of particular analytes. This need ranges from the basic science research lab, where biochemical pathways are being mapped out and their functions correlated to disease processes, to clinical diagnostics, where patients are routinely monitored for levels of clinically relevant analytes. Other areas include pharmaceutical research and drug discovery applications, DNA testing, military applications such as biowarfare monitoring, veterinary, food, and environmental applications. In all of these cases, the presence and quantity of a specific analyte or group of analytes, needs to be determined.

For analysis in the fields of pharmacology, genetics, chemistry, biochemistry, biotechnology, molecular biology and numerous others, it is often useful to detect the presence of one or more molecular structures and measure interactions between molecular structures. The molecular structures of interest typically include, but are not limited to, cells, antibodies, antigens, metabolites, proteins, drugs, small molecules, enzymes, nucleic acids, and other ligands and analytes. In medicine, for example, it is very useful to determine the existence of a cellular constituents such as receptors or cytokines, or antibodies and antigens which serve as markers for various disease processes, which exists naturally in physiological fluids or which has been introduced into the system. In genetic analyses, fragment DNA and RNA sequence analysis is very useful in diagnostics, genetic testing and research, agriculture, and pharmaceutical development. Because of the rapidly advancing state of molecular cell biology and understanding of normal and diseased systems, there exists an increasing need for methods of detection, which do not require labels such as fluorophores or radioisotopes, are quantitative and qualitative, specific to the molecule of interest, highly sensitive and relatively simple to implement. Many known targets such as orphan drug receptors, and many more targets becoming available, have no known affinity ligands, so that unlabeled means of detecting molecular interactions are highly desirable. In addition, the reagent costs for many labeled assay technologies are quite expensive, in addition to the economic and environmental costs of disposing of toxic fluorophores and radioisotopes.

Numerous methodologies have been developed over the years to meet the demands of these fields, such as Enzyme-Linked Immunosorbent Assays (ELISA), Radio-Immunoassays (RIA), numerous fluorescence assays, mass spectroscopy, colorimetric assays, gel electrophoresis, as well as a host of more specialized assays. Most of these assay techniques require specialized preparations, especially attaching a label or greatly purifying and amplifying the sample to be tested. To detect a binding event between a ligand and an antiligand, a detectable signal is required which relates to the existence or extension of binding. Usually the signal is provided by a label that is conjugated to either the ligand or antiligand of interest. Physical or chemical effects which produce detectable signals, and for which suitable labels exist, include radioactivity, fluorescence, chemiluminescence, phosphorescence and enzymatic activity to name a few. The label can then be detected by spectrophotometric, radiometric, or optical tracking methods. Unfortunately, in many cases it is difficult or even impossible to label one or all of the molecules needed for a particular assay. Also, the presence of a label may make the molecular recognition between two molecules not function for many reasons including steric effects. In addition, none of these labeling approaches determines the exact nature of the binding event, so for example active site binding to a receptor is indistinguishable from non-active-site binding such as allosteric binding, and thus no functional information is obtained via the present detection methodologies. Therefore, a method to detect binding events that both eliminates the need for the label as well as yields functional information would greatly improve upon the above mentioned approaches.

Other approaches for studying biochemical systems have used various types of dielectric measurements to characterize certain classes of biological systems such as tissue samples and cellular systems. In the 1950's, experiments were conducted to measure the dielectric properties of biological tissues using standard techniques for the measurement of dielectric properties of materials known at the time. Since then various approaches to carrying out these measurements have included frequency domain measurements, and time domain techniques such as Time Domain Dielectric Spectroscopy. In these approaches, the experiments were commonly carried out using various types of coaxial transmission lines, or other transmission lines and structures of typical use in dielectric characterization of materials. This included studies to look at the use and relevance of the dielectric properties of a broad range of biological systems: The interest has ranged from whole tissue samples taken from various organs of mammalian species, to cellular and sub-cellular systems including cell membrane and organelle effects. Most recently, there have been attempts to miniaturize the above-mentioned techniques (see e.g., U.S. Pat. Nos. 5,653,939; 5,627,322 and 5,846,708) for improved detection of changes in the dielectric properties of molecular systems. These configurations have several drawbacks, including some substantial limitations on the frequencies useable in the detection strategy, and a profound limitation on the sensitivity of detecting molecular systems, as well as being expensive to manufacture.

In general, limitations exist in the areas of specificity and sensitivity of most assay systems. Cellular debris and non-specific binding often cause the assay to be noisy, and make it difficult or impossible to extract useful information. As mentioned above, some systems are too complicated to allow the attachment of labels to all analytes of interest, or to allow an accurate optical measurement to be performed. Further, a mentioned above, most of these detection technologies yield no information on the functional nature of the binding event. Therefore, a practical and economical universal enabling which can directly monitor without a label, in real time, the presence of analytes or the extent, function and type of binding events and other interactions that are actually taking place in a given system would represent a significant breakthrough.

More specifically, the biomedical industry needs an improved general platform technology which has very broad applicability to a variety of water-based or other fluid-based physiological systems, such as nucleic acid binding, protein-protein interactions, small molecule binding, as well as other compounds of interest. Ideally, the assay should not require highly specific probes, such as specific antibodies and exactly complementary nucleic acid probes; it should be able to work in native environments such as whole blood, cytosolic mixtures, as well as other naturally occurring systems; it should operate by measuring the native properties of the molecules, and not require additional labels or tracers to actually monitor the binding event; for some uses it should be able to provide certain desired information on the nature of the binding event, such as whether or not a given compound acts as an agonist or an antagonist on a particular drug receptor, and not function simply as a marker to indicate whether or not the binding event has taken place. For many applications, it should be highly miniaturizable and highly parallel, so that complex biochemical pathways can be mapped out, or extremely small and numerous quantities of combinatorial compounds can be used in drug screening protocols. In many applications, it should further be able to monitor in real time a complex series of reactions, so that accurate kinetics and affinity information can be obtained almost immediately. Perhaps most importantly, for most commercial applications it should be inexpensive and easy to use, with few sample preparation steps, affordable electronics and disposable components, such as surface chips for bio-assays that can be used for an assay and then thrown away, and be highly adaptable to a wide range of assay applications.

It is important to note that other industries have similar requirements for detection, identification or additional analysis. While most applications involve the use of biological molecules, virtually any molecule can be detected if a specific binding partner is available or if the molecule itself can attach to the surface as described below.

The present invention fulfills many of the needs discussed above and other needs as well.

SUMMARY OF THE INVENTION

The present invention provides test systems and bio-assay devices which can be used to detect and identify molecular binding events. In one embodiment, the invention provides a test system having a test fixture, a measurement system, and a computer. The test fixture includes a bio-assay device having a signal path and a retaining structure configured to place a sample containing molecular structures in electromagnetic communication with the signal path. The measurement system is configured to transmit test signals to and to receive test signals from the signal path at one or more predefined frequencies. The computer is configured to control the transmission and reception of the test signals to and from the measurement system.

The invention will be better understood when considered in light of the foregoing drawings and detailed description.

DESCRIPTION OF EXEMPLARY EMBODIMENTS

Figure 1A:
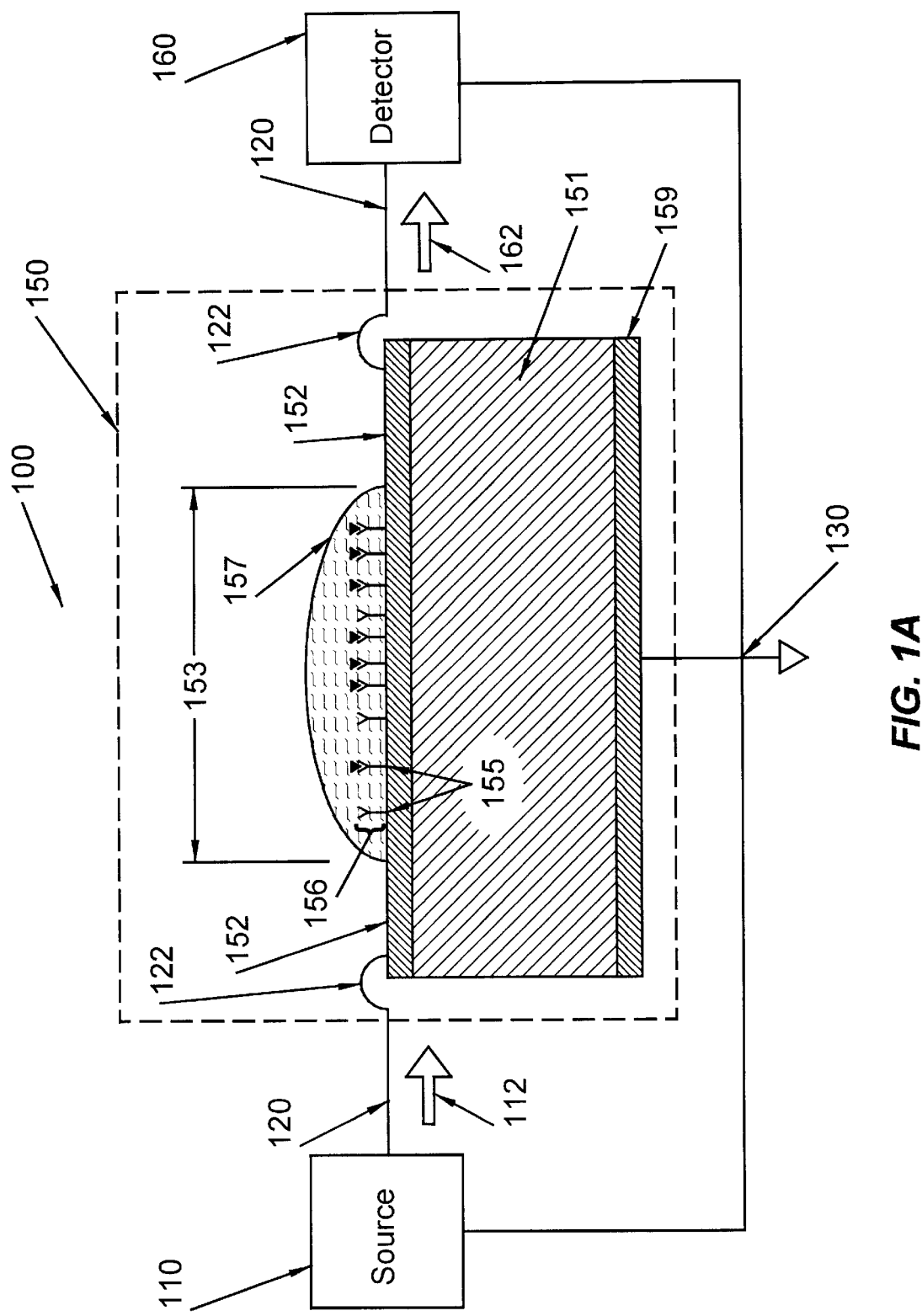
FIG. 1A illustrates one embodiment of a bio-assay system in accordance with the present invention.

Table of Contents
 I. Definitions
 II. General Overview
 III. Single Path Test System and Bio-Assays
  A. Test System
  B. Test Fixture
  C. Bio-Assay Devices
 IV. Array Test System and Bio-Assays
  A. Test System
  B. Test Fixture
  C. Bio-Assay Devices
 V. Applications
  A. Drug Discovery Application
  B. Nucleic Acid Chemistry Application
I. Definition of Terms As used herein, the terms biological "binding partners" or "ligand/antiligand" or "ligand/antiligand complex" refers to molecules that specifically recognize other molecules to form proximal complexes such as antibody-antigen, lectin-carbohydrate, nucleic acid-nucleic acid, protein-protein, protein-small molecule such as drug-receptor, etc. Biological binding partners need not be limited to pairs of single molecules. Thus, for example, a single ligand may be bound by the coordinated action of two or more "anti-ligands".

As used herein, the term "ligand" or "analyte" or "marker" refers to any molecule being detected. It is detected through its interaction with an antiligand, which specifically or non-specifically binds the ligand, or by the ligand's characteristic dielectric properties. The ligand is generally defined as any molecule for which there exists another molecule (i.e. an antiligand) which specifically or non-specifically binds to said ligand, owing to recognition, chemical or otherwise, of some portion of said ligand. The antiligand, for example, can be an antibody and the ligand a molecule such as an antigen which binds specifically to the antibody. In the event that the antigen is bound to the surface and the antibody is the molecule being detected, for the purposes of this document the antibody becomes the ligand and the antigen is the antiligand. The ligand may also consist of nucleic acids, proteins, lipids, small molecules, membranes, carbohydrates, polymers, cells, cell membranes, organelles and synthetic analogues thereof.

Suitable ligands for practice of this invention include, but are not limited to antibodies (forming an antibody/epitope complex), antigens, nucleic acids (e.g. natural or synthetic DNA, RNA, gDNA, cDNA, mRNA, tRNA, etc.), lectins, sugars (e.g. forming a lectin/sugar complex), glycoproteins, receptors and their cognate ligand (e.g. growth factors and their associated receptors, cytokines and their associated receptors, signaling receptors, etc.), small molecules such as drug candidates (either from natural products or synthetic analogues developed and stored in combinatorial libraries), metabolites, drugs of abuse and their metabolic by-products, co-factors such as vitamins and other naturally occurring and synthetic compounds, oxygen and other gases found in physiologic fluids, cells,.cellular constituents cell membranes and associated structures, other natural products found in plant and animal sources, other partially or completely synthetic products, and the like.

As used herein, the term "antiligand" refers to a molecule which specifically or nonspecifically binds another molecule (i.e., a ligand). The antiligand is also detected through its interaction with a ligand to which it specifically binds or by its own characteristic dielectric properties. As used herein, the antiligand is usually immobilized on the surface, either alone or as a member of a binding pair that is immobilized on the surface. In some embodiments, the antiligand may consist of the molecules on the signal path, on a dielectric surface or in a dielectric volume, or a conductive surface. The antiligand may further be attached by one or more linkers to a surface or matrix proximal to, or incorporated in, the signal path. Alternatively, once an antiligand has bound to a ligand, the resulting antiligand/ligand complex can be considered an antiligand for the purposes of subsequent binding or other subsequent interactions.

As used herein, the term "specifically binds" when referring to a protein or polypeptide, nucleic acid, or receptor or other binding partners described herein, refers to a binding reaction which is determinative of the cognate ligand of interest in a heterogeneous population of proteins and/or other biologics. Thus, under designated conditions (e.g. immunoassay conditions in the case of an antibody, or stringent conditions in the case of nucleic acid binding), the specified ligand binds to its particular "target" (e.g. a hormone specifically binds to its receptor, or a given nucleic acid sequence binds to its complementary sequence) and does not bind in a significant amount to other molecules present in the sample or to other molecules to which the ligand or antibody may come in contact in an organism or in a sample derived from an organism.

As used herein, the terms "isolated" "purified" or "biologically pure" refer to material which is substantially or essentially free from components that normally accompany it as found in its native state.

As used herein, the term "nucleic acid" refers to a deoxyribonucleotide or ribonucleotide polymer in either single-or double-stranded form, and unless otherwise limited, encompasses known analogs of natural nucleotides that can function in a similar manner as naturally occurring nucleotides.

As used herein, the terms "polypeptide", "peptide" and "protein" are used interchangeably to refer to a monomer or polymer of amino acid residues. The terms apply to amino acid polymers in which one or more amino acid residue is an artificial chemical analogue of a corresponding naturally occurring amino acid, as well as to naturally occurring amino acid polymers.

As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to VH-CH1 by a disulfide bond. The F (ab)'$_2$ may be reduced under mild conditions to break the disulfide linkage in the hinge region thereby converting the (Fab') 2 dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH:VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879–5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the terms "immunological binding" and "immunological binding properties" refer to the non-covalent interactions of the type which occur between an immunoglobulin molecule and an antigen for which the immunoglobulin is specific. As used herein, a biological sample is a sample of biological tissue or fluid that, in a healthy and/or pathological state, that is to be assayed for the analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect the analyte(s) of interest in samples from any mammal, such as dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

As used herein, the term "receptor" or "drug receptor" refers to a biological structure that is a target for drug therapy, and includes proteins such as membrane-bound structures like G-protein Coupled Receptors, nuclear receptors like hormone receptors; proteins which modulate the expression of genes, such as promoters and inducers; nucleic acid targets such as genes, expressed sequences, regulatory and signaling sequences; other proteins in biological systems which modulate or mediate physiological activities of a given organism.

As used herein, the term "signal path" refers to a transmission medium long or through the bio-electrical interface which is capable of supporting an electromagnetic signal of any useful frequency including a DC static field. A non-exhaustive list of signal paths include conductive and dielectric waveguide structures, conductive and dielectric transmission line structures, multiple-conductor and multiple dielectric transmission mediums such as transverse electromagnetic (TEM) transmission lines, transmission lines with three or more conductive or dielectric elements which support Transverse Electric (TE), Transverse Magnetic (TM), or TEM modes of propagation such as quadrupolar and octupolar lines; coupled waveguides and conductive and dielectric resonant cavity structures which may or may not be coupled; conductive and dielectric antenna structures such as dipole and quadrupole antennas; evanescent wave structures such as evanescent waveguides, both coupled and uncoupled, evanescent wave transmission lines, and evanescent wave antennas; other non-modal structures like wires, printed circuits, and other distributed circuit and lumped impedance conductive structures, and the like. In embodiments in which the signal path consists of a conductive region or regions, the conductive region extends continuously over that range. In embodiments in which the signal path is non-metallic, e.g., a dielectric waveguide, antenna, or transmission line, the signal path is defined as the path having either the greatest conductivity at the frequency or range of frequencies being used, or as the molecular binding region itself.

As used herein, the term "molecular binding region" or "MBR" refers to a surface layer or a volume element having of at least one molecular structure (i.e., an analyte, antiligand, or a ligand/antiligand pair, etc.) coupled to the signal path along or between the bio-electrical interface. The molecular binding region may consist of one or more ligands, antiligands, ligand/antiligand complexes, linkers, matrices of polymers and other materials, or other molecular structures described herein. Further, the molecular binding region may be extremely diverse and may include one or more components including matrix layers and/or insulating layers, which may have one or more linking groups. The molecular binding region is coupled to the signal path either via a direct or indirect physical connection or via electromagnetic coupling when the ligand is physically separated from the signal path. The molecular binding region may be of a derivatized surface such as by thiol linkers, alkanethiols, heterobifunctional alkanes, branched dextrans, biotinylated metals and the like, all in accordance with standard practice in the art.

As used herein, the term "binding event" refers to an interaction or association between two or more molecular structures, such as a ligand and an antiligand. The interaction may occur when the two molecular structures as are in direct or indirect physical contact or when the two structures are physically separated but electromagnetically coupled. Examples of binding events of interest in a biological context include, but are not limited to, ligand/receptor, antigen/antibody, drug-receptor, protein-protein, enzyme/substrate, DNA/DNA, DNA/RNA, RNA/RNA, nucleic acid mismatches, complementary nucleic acids and nucleic acid/proteins. Alternatively, the term "binding event" may refer to a single molecule or molecular structure described herein, such as a ligand, or an antiligand/ligand complex, which is bound to the signal path. In this case the signal path is the second molecular structure.

As used herein, the term "ligand/antiligand complex" refers to the ligand bound to the antiligand. The binding may be specific or non-specific, and the bonds are typically covalent bonds, hydrogen bonds, immunological binding, Van der Waals forces, or other types of binding.

As used herein, the term "coupling" refers to the transfer of energy between two structures either through a direct or indirect physical connection or through any form of signal coupling, such as electrostatic or electromagnetic coupling, matter-field interactions, and the like.

As used herein, the term "test signal" refers to a d.c, frequency domain, or time domain signal used to probe the bio-assay device. Frequency domain signals may propagate at any useful frequency defined within the electromagnetic spectrum. For example, the frequency range within which a test signal may propagate is for example at or above 1 MHz, such as 5 MHz 10 MHz, 20 MHz, 45 MHz, 100 MHz, 500 MHz, 1 GHz, 5 GHz, 10 GHz, 30 GHz, 50 GHz, 100 GHz, 500 GHz, 1000 GHz and frequencies ranging therebetween. Time domain test signals may be generated in square, sawtooth, triangle, or other known waveforms and propagate at periodic or aperiodic intervals, Time domain signals may consist of amplitudes and rise/fall times which permit modulation which coupled to the molecular binding region. For example, a time domain test signal may consist of a square waveform having an amplitude between 0V and 50V, and a rise/fall time of between 0.1 pS and 1 uS, or range anywhere therebetween.

As used herein, the term "enzyme," refers to a protein which acts as a catalyst to reduce the activation energy of a chemical reaction in other compounds or "substrates", but is not a final product in the reaction.

As used herein, the term "sample" and/or "solution" includes a material in which a ligand resides. A non-exhaustive list of solutions includes materials in solid, liquid or gaseous states. Solid solutions may be comprised of naturally-occurring or synthetic molecules including carbohydrates, proteins, oligonucleotides, or alternatively, any organic polymeric material, such as nylon, rayon, dacryon, polypropylene, teflon, neoprene, delrin or the like. Liquid solutions include those containing an aqueous, organic or other primary components, gels, gases, and emulsions. Exemplary solutions include celluloses, dextran derivatives, aqueous solution of d-PBS, Tris buffers, deionized water, blood, physiological buffer, cerebrospinal fluid, urine, saliva, water, organic solvents. The solution is used herein to refer to the material in which the ligand and/or antiligand are applied to the binding surface. The solution contains the sample to be analyzed.

As used herein, the term "linking group" or "linker" refers to chemical structures which are used to attach any two components on the bio-assay device. The linking groups thus have a first binding portion that binds to one component, such as a conductive surface or dielectric matrix, and have a second binding portion that binds to another component such as the matrix or the antiligand.

As used herein, the term "bio-assay device" refers to a structure on which the molecular binding region is formed. The bio-assay device may consist of a surface, recessed area, volume, or a hermetically sealed enclosure, each of which may be any particular size or shape.

As used herein, the "bio-assay system" refers to the bio-assay device as described above, in connection with the components necessary to electromagnetically probe and detect the bio-assay device. These components include, but are not limited to, the signal path(s), substrate(s), electronic devices such as signal generators, oscilloscopes, network analyzers, time domain reflectometers or other equipment necessary to probe and detect signals from the bio-assay device, microchips and microprocessors which can probe and detect electromagnetic signals and analyze data, and the like.

As used herein, the term "resonant" or "resonance" refers generally to a rapidly changing dielectric response as a function of frequency.

As used herein, the term "dispersion" refers to the functional dependence of the dielectric properties of a material on the frequency of the probing radiation, and in particular is used to distinguish regions of the electromagnetic spectrum in which the dielectric properties of a given material has a strong functional dependence on the frequency of the probing electromagnetic energy.

As used herein, "bio-electrical interface" refers to an interface region which includes the signal path for supporting test signal propagation and the molecular binding region of a sample.

As used herein, the term "matrix" or "binding matrix" refers to a layer or volume of material on the bio-assay chip that is used as a spacer or to enhance surface area or volume available for binding or to optimize orientation of molecules for enhanced binding, or to enhance any other property of binding so as to optimize the bio-assay device. The matrix layer may be comprised or carbohydrates such as dextran, poly amino acids, cross-linked and non-cross linked proteins, and the like.

As used herein, the term "structural change" refers to any change of position, chemical make-up, orientation, conformation, relative orientation of sub-structures or sub-units of a molecule or molecular system. A non-exhaustive list includes conformational changes, dimerization and polymerization, covalent binding, sub-unit motion, interactions with other molecules such as covalent and non-covalent binding, hydrophobic bonding, denaturation and re-naturation, hybridization, ionization, substitution, and the like.

II. General Overview of the Bio-Assay System

The present invention makes use of the observation that a vast number of molecules can be distinguished based upon the unique dielectric properties most molecules exhibit. These distinguishing dielectric properties can be observed by coupling an electromagnetic signal to the bound molecular structure. The unique dielectric properties modulate the signal, giving it a unique signal response. The unique signal response can then be used to detect and identify the ligands and other molecules which make up the molecular binding region.

FIG. 1A illustrates a side view of one embodiment of a bio-assay system 100 in accordance with the present invention. The system 100 is illustrated in a two conductor, signal-plane ground-plane, circuit topology which may be realized in a multitude of architectures including lumped or distributed element circuits in microstrip, stripline, coplanar waveguide, slotline or coaxial systems. Moreover, those of skill in the art of electronics will readily appreciate that the system may be easily modified to a single conductor waveguide system, or a three or more conductor system.

As illustrated, the system 100 includes a signal source 110, transmission lines 120, a source/detector ground plane 130, a bio-assay device 150, and a signal detector 160. The illustrated embodiment shows two transmission lines 120 coupled to the bio-assay device 150, although in an alternative embodiment, the system may consist of a single transmission line coupled to the bio-assay device for making a single port measurement. Further alternatively, three or more transmission lines may be coupled to the bio-assay device 150 for multiple port measurements.

Transmission lines 120 are formed from a material which can support the propagation of a D.C voltage/current or an A.C. time or frequency domain signal over the desired frequency of operation. Transmission lines 120 may be realized as a conductive layer, such as a center conductor in a coaxial cable or a gold transmission line. deposited on a substrate, such as alumina, diamond, sapphire, polyimide, or glass using conventional photolithography or semiconductor processing techniques. Signal interconnections 122 may be made via wire/ribbon bonds, soldering, conductive epoxy, connectors, or other conventional connection techniques appropriate for the frequency of operation.

The system 100 further includes a bio-assay device 150 which includes a dielectric substrate 151 and a signal path 152. The dielectric substrate 151 may consists of any insulating material such as glass, alumina, diamond, sapphire, silicon, gallium arsenide or insulating materials used in semiconductor processing. Alternatively, dielectric material such as RT/Duroid® manufactured by the Rodgers Corporation or other similar dielectric materials may be used.

The signal path 152 is designed to provide a low insertion loss medium and can consist of any TE, TM, or TEM signal architecture. In an exemplary embodiment, the signal path 152 consists of a photolithographically formed microstrip transmission line having a sputtered gold thickness on the order of between 0.1 um to 1000 um. In this embodiment, the transmission line is designed to provide low signal loss from D.C. to 110 GHz. Other conductive materials such as indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof may be used to form the transmission line. In another embodiment, the signal path 152 consists of a dielectric region, further described below.

A bio-electrical interface region 153 defines the region over the signal path 152 and the MBR 156 of the applied sample 157 are electromagnetically coupled. In one embodiment of the invention, the MBR 156 specifically binds to the signal path 152. In another embodiment of the invention, the MBR 156 binds non-specifically to the signal path 152. In still another embodiment of the invention, the MBR is electromagnetically coupled to, but is separate from the signal path 152. Sufficient electromagnetic coupling may occur either through direct binding to the signal path 152 or from the molecular structures of the MBR 156 being suspended in close proximity to the signal path 152. When direct molecular binding to the signal path is sought, the signal path may include linker and/or matrix layers as further described in the commonly-owned, co-pending U.S. patent application entitled "Method and Apparatus for Detecting Molecular Binding Events," Ser. No. 09/243,194, filed Feb. 2, 1999 incorporated herein by reference.

The MBR 156 is primarily composed of one or more ligands, although other molecules and structures may also be included, as described herein. The MBR 156 may consist of only one bound ligand tier, for instance in the case of primary binding, or it may consist of two, three, four, five or more bound ligand tiers, in the instances where there are secondary or higher-order binding events occurring. Multiple ligand tiers may occur at different binding surfaces 155 over the same signal path. Additionally, the MBR 156 may comprise a matrix in a volume, with ligands and antiligands attached to structural components such as branched dextran, polymers, amino acid chains, other linkers known in the art, and the like.

In the illustrated embodiment, dielectric substrate 151 is located between the signal path 152 and the bio-assay ground plane 159. However, the MBR 156 and sample 157 may be located proximate to the bio-assay ground plane 159 such that MBR 156 is electromagnetically coupled to the bio-assay ground plane 159 alternatively or in addition to the MBR's location to the signal path 152 as shown in FIG. 1A.

The system 100 includes a signal source 110 which launches a test signal 112 onto the transmission line 120 and towards the bio-assay device 150. A signal detector 160 is positioned along the transmission path to receive the modulated test signal 162 (either reflected or transmitted or both). When the test signal 112 propagates along the bio-electrical interface region 153 of the bio-assay device 150, the dielectric properties of the MBR 156 modulate the test signal. The modulated test signal 162 is then recovered by the detector 160 and used to detect and identify the molecular binding events occurring within the MBR 156.

Figure 1B:
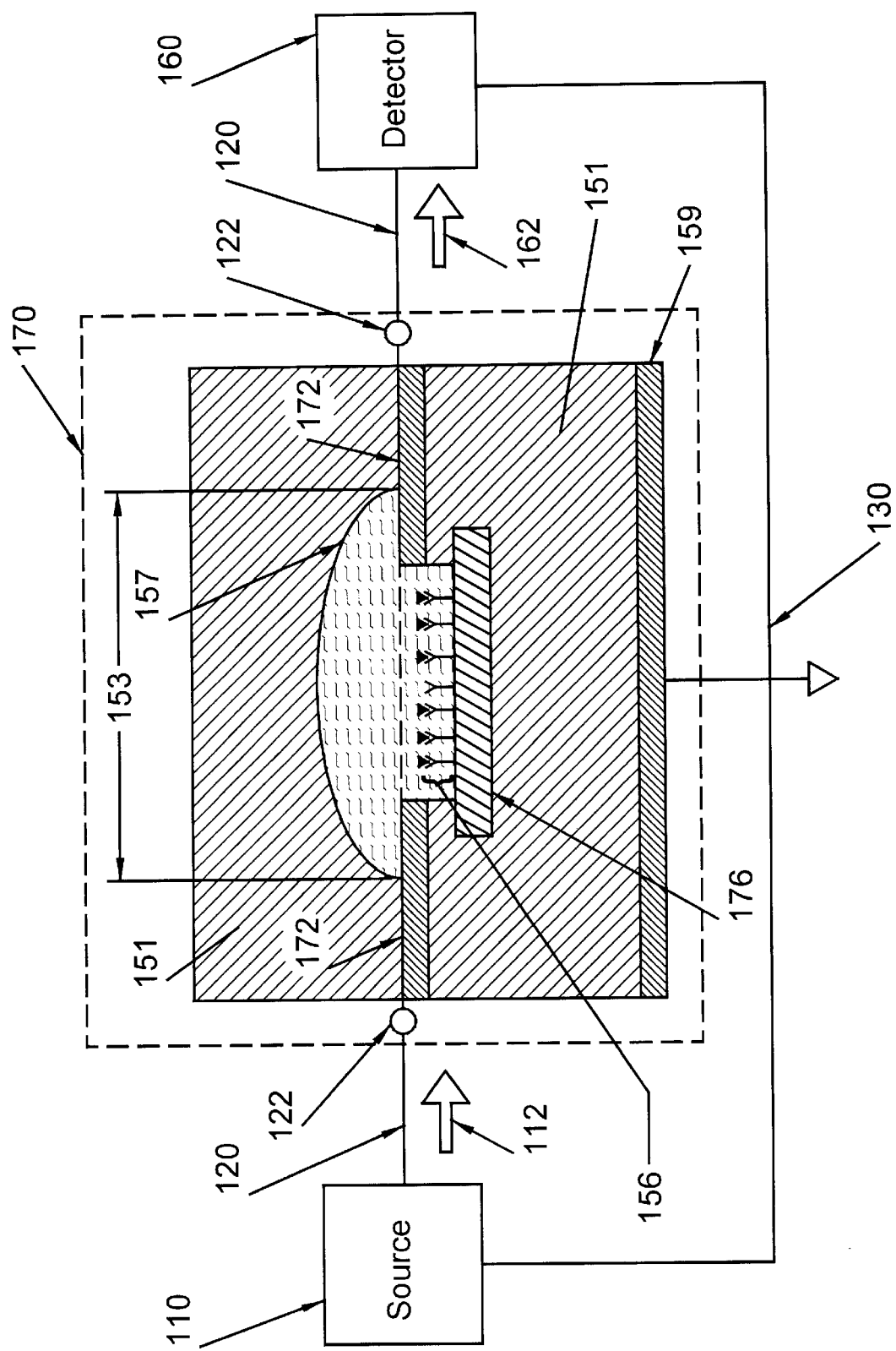
FIG. 1B illustrates a second embodiment of a bio-assay system in accordance with the present invention.

FIG. 1B illustrates a second embodiment of the bio-assay test system in accordance with the present invention. Reference numbers used in FIG. 1A are reused to indicate previously described elements. The system includes the described signal source 110, transmission lines 120, connections 122, ground plane 130, bio-assay device 150 and signal detector 160.

The bio-assay device 170 includes a dielectric substrate 151 and ground plane 159, previously described. The signal path includes transmission lines 172 and a dielectric region 156 formed across the bio-electrical interface region 153 between transmission lines 120. The dielectric region 156 is composed of the MBR and formed from the molecular binding events of the sample 157. The dielectric region is designed to provide a DC-blocked, low signal loss medium between transmission lines 172. The D.C. blocking properties of the dielectric region 156 prevents D.C. voltages and currents from passing between the input and output which could interfere with the operation of the test system, further described below. Dielectric region 156 provides low signal loss over the desired testing frequencies, some examples being 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween.

As described above, the MBR operates to modulate the test signal. The architecture of the dielectric region 156 serves to signal support propagation through the bio-electrical interface region without high signal loss. An insulating substrate 176 is used as a binding surface for the MBR in order to form the dielectric region 156 and the MBR may bind either specifically or non-specifically to the insulating substrate 176. The insulating substrate 176 may consist of the same or different dielectric material as the dielectric substrate 151 and may, alternatively or in addition, consist of linker, matrix, and/or insulating layers further described in the incorporated patent application entitled: "Method and Apparatus for Detecting Molecular Binding Events," Ser. No. 09/243,194.

The length of the dielectric region (MBR) 156 is selected to provide sufficient test signal modulation while minimizing through loss. Typical lengths are on the order of $10^{-1}$ m, $10^{-2}$ m $10^{-3}$ m, $10^{-4}$ m, $10^{-5}$ m, $10^{-6}$ m, $10^{-7}$ m, $10^{-8}$ m, $10^{-9}$ m, $10^{-10}$m, $10^{-11}$ m, or range anywhere therebetween.

As indicated, detection and identification of a ligand is also possible when the ligand is physically separated from but electromagnetically coupled to the signal path 152. In this instance, the coupling between the signal path 153 and the suspended ligand will alter the response of the test signal propagating along the signal path 152, thereby providing a means for detecting and/or identifying it the suspended ligand. The maximum separation between the signal path 151 and suspended ligand is influenced by such factors as the effective dielectric constant of the medium between the signal path 151 and the ligand, the total coupling area, the sensitivity of the signal detector, concentration of the ligands in solution, and the desired detection time. Separation distances are typically on the order of $10^{-1}$ m, $10^{-2}$ m $10^{-3}$ m, $10^{-4}$ m, $10^{-5}$ m, $10^{-6}$ m, $10^{-7}$ m, $10^{-8}$ m, $10^{-9}$ m, $10^{-10}$ m or range anywhere therebetween.

In some embodiments, such as cell based assays, the MBR 156 may be electromagnetically coupled to the signal path 151 through the sample. Thus, cells, and in particular cell membranes and membrane-based structures may couple to the signal path indirectly.

III. Single Path Test System and Bio-assay

Molecular binding events occurring within the MBR may be detected and identified using various test systems which generate, recover, and subsequently analyze changes in the generated test signal. Test systems which are capable of use with the present invention include those systems designed to detect changes in the signal's voltage, current, impedance, admittance, reactance, amplitude, phase, delay, frequency, wave shape and/or timing, and other signal properties.

A. Test System

Figure 2:
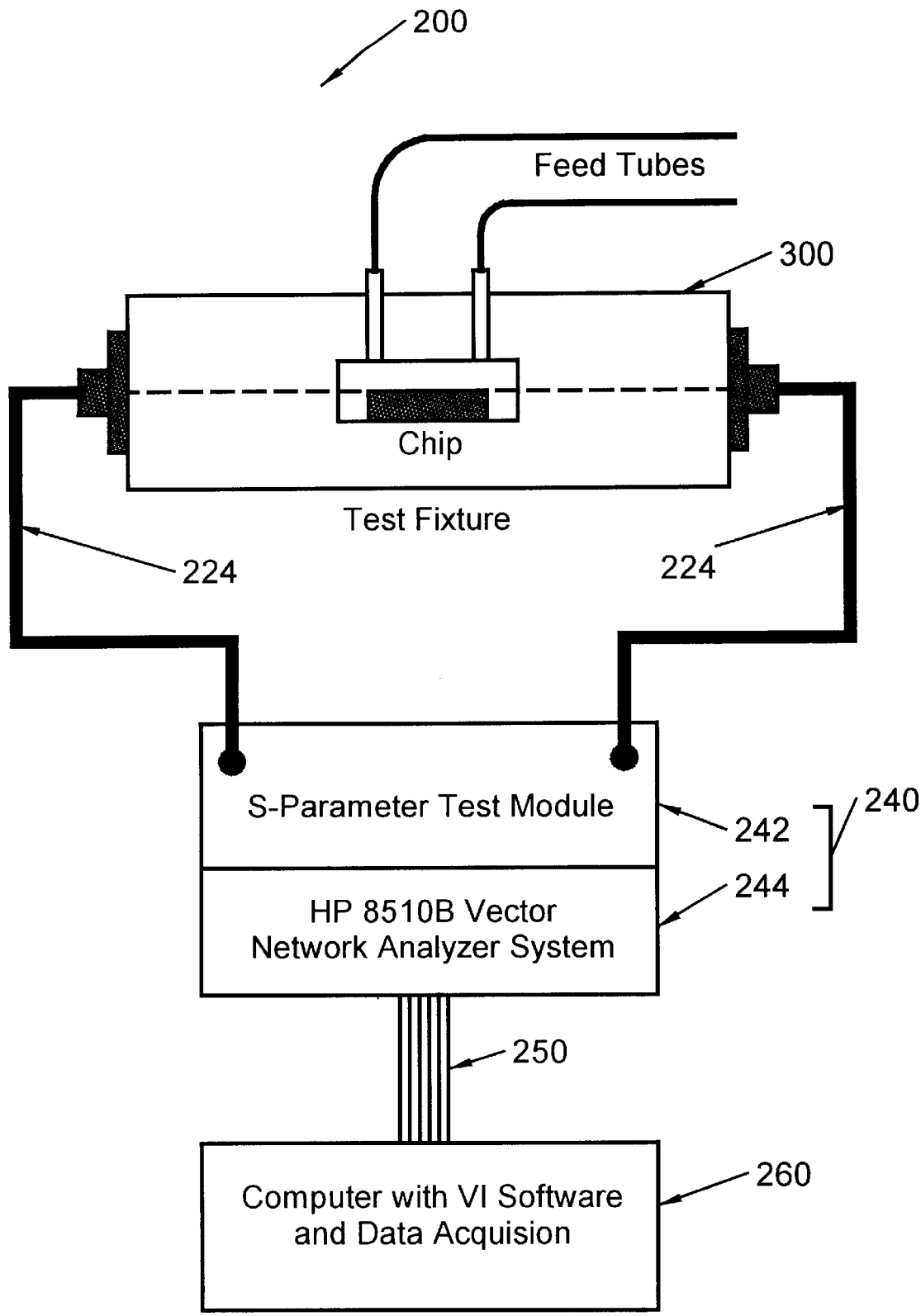
FIG. 2 illustrates one possible embodiment of a single path test system in accordance with the present invention.

FIG. 2 illustrates one possible embodiment of a single path test system 200 in accordance with the present invention. The test system includes a test fixture 300, further described below, a measurement system 240 and a computer 260. Measurement system 240 communicates test signals to and from test fixture 300 via test cables 224. Computer 260 controls measurement system 240 via a control bus 250.

In one embodiment, measurement system 240 includes an S-Parameter Test Module model no. 8516A 242, a Frequency Synthesizer (not shown) model no. 8341B, and a Vector Network Analyzer model no. 8510B 244, all of which are manufactured by the Hewlett Packard Company of Palo Alto, Calif. (www.hp.com). In this embodiment, measurement system 240 provides a measurement capability between the frequencies of 45 MHz and 40 GHz. In an alternative embodiment, measurement system 240 may consist of model number HP 8751A network analyzer which provides a measurement capability between 5 Hz and 500 MHz. In a further embodiment, measurement system may consist of model number HP 85106D which provides a measurement capability between 33 GHz and 110 GHz, both manufactured by the Hewlett Packard Company. Other measurement systems such as scalar network analyzers, Time Domain Reflectometers, another similar measurement systems may also be used to detect a change in the test signal which is attributable to the dielectric properties of the MBR.

Test cables 224 support the propagation of the test signals at the desired frequency. In one embodiment, test cables consists of model number 6Z PhaseFlex™ Microwave test cables manufactured by the W. L. Gore and Associates, Inc. of Newark Del. (www.gore.com). Control bus 250 provides communication between the test system and computer 260 and in the illustrated embodiment consists of a General Purpose Instrument Bus (GPIB). In alternative embodiments, measurement system 240 and computer 260 may be integrated within a single automated measurement unit.

Computer 260 controls measurement system 240 to generate test signals at one or more frequencies, output power levels, signal shapes, phase offsets or other measurement settings. In the preferred embodiment, computer 260 includes a+450 MHz microprocessor, such as those manufactured by the Intel Corporation of Santa Clara, Calif. (www.intel.com). Test system control, data acquisition, and analysis may be performed using a graphical programming software tool, such as LabVIEW® manufactured by the National Instruments Corporation of Austin, Tex. (www.natinst.com).

Alternatively or in addition, measurement system 240 may include a Time Domain Reflectometer (TDR) system, such as those optionally available with the above-described network analyzers or described in the incorporated patent application entitled: "Method and Apparatus for Detecting Molecular Binding Events," Ser. No. 09/243,194. Essentially, TDR systems transmit a signal pulse towards a unit under test. The return signal (either reflected from or transmitted through the unit under test) can be analyzed to ascertain information about the unit under test. Specifically in the present embodiment, the dielectric properties of the MBR will modulate the signal pulse, thereby enabling detection and identification of the molecular binding events therein.

TDR measurements may be made at the fixture level using the aforementioned systems, or at the bio-assay device level utilizing one or more of the standard techniques of microwave monolithic circuit (MMIC) technologies. When a TDR measurement is made at the device level, a time-domain test signal is generated in close proximity to the bio-assay device. This signal is then propagated along the signal path to the bio-assay element via standard conductive geometries used in MMIC technologies. The molecular binding region modulates the time-domain test signal, and the modulated signal is then recovered to be analyzed.

B. Test Fixture

The test fixture of the present invention is designed to provide a signal path and to secure the MBR of the applied sample in direct contact with or in close proximity to the signal path such that a test signal propagating therealong will electromagnetically couple to the MBR. The test fixture may consist of a wholely or partially enclosed, or recessed structure over or into which the sample may be deposited, injected, or otherwise applied.

Figure 3A:
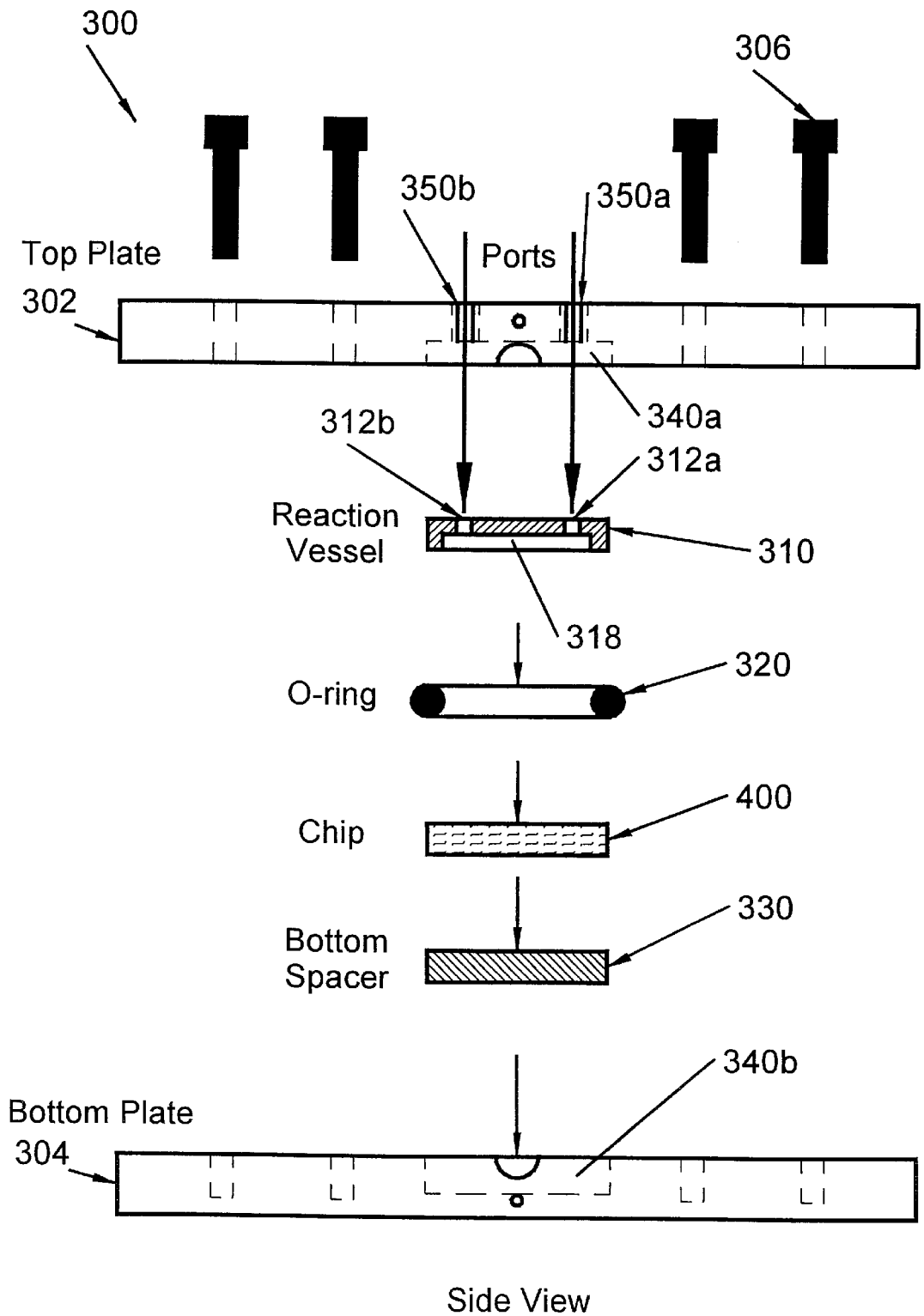
FIGS. 3A–3I illustrate various views of a test fixture in accordance with the present invention.

FIG. 3A illustrates in a side view one possible embodiment of the test fixture 300 in accordance with the present invention. Test assembly fixture 300 includes a top plate 302 and a bottom plate 304. Top plate 302 includes ports 350a and 350b for injecting the sample solution. Top plate 302 further includes the top half of a sample cavity 340a. Bottom plate 304 includes the bottom half of the sample cavity 340b. In the preferred embodiment, top and bottom plates 302 and 304 are each composed of machined stainless steel and each measures 0.0320 cm×1.575 cm×3.15 cm. Screws 306 are used to attach top and bottom plates 302 and 304.

Contained with the sample cavity 340 is a reaction vessel 310, an O-ring 320, a bio-assay device 400 (further described in FIG. 4 below), and a bottom spacer 330. Reaction vessel 310 includes ports 312a and 312b for receiving the sample. Reaction vessel 310 further includes an O-ring cavity 318 for accommodating the O-ring 320. O-ring 320 is positioned between the reaction vessel 310 and the bio-assay device 400 to secure the sample along the bio-assay device 400. Bio-assay device 400 provides the signal path and bioelectrical interface along which the MBR will form. Bottom spacer 330 is provided to elevate the bio-assay device 400 to the proper height so that it may couple to input and output transmission lines (not shown) formed between the top and bottom plates 302 and 304.

The sample is injected into sample cavity 340 via feed tubes (not shown) coupled to ports 350a and 350b. Sample flows through reaction vessel ports 312a and 312b into the reaction vessel 310. In the preferred embodiment, the sample is injected by applying positive pressure in one feed tube and negative pressure to the other feed tube.

Figure 3B:
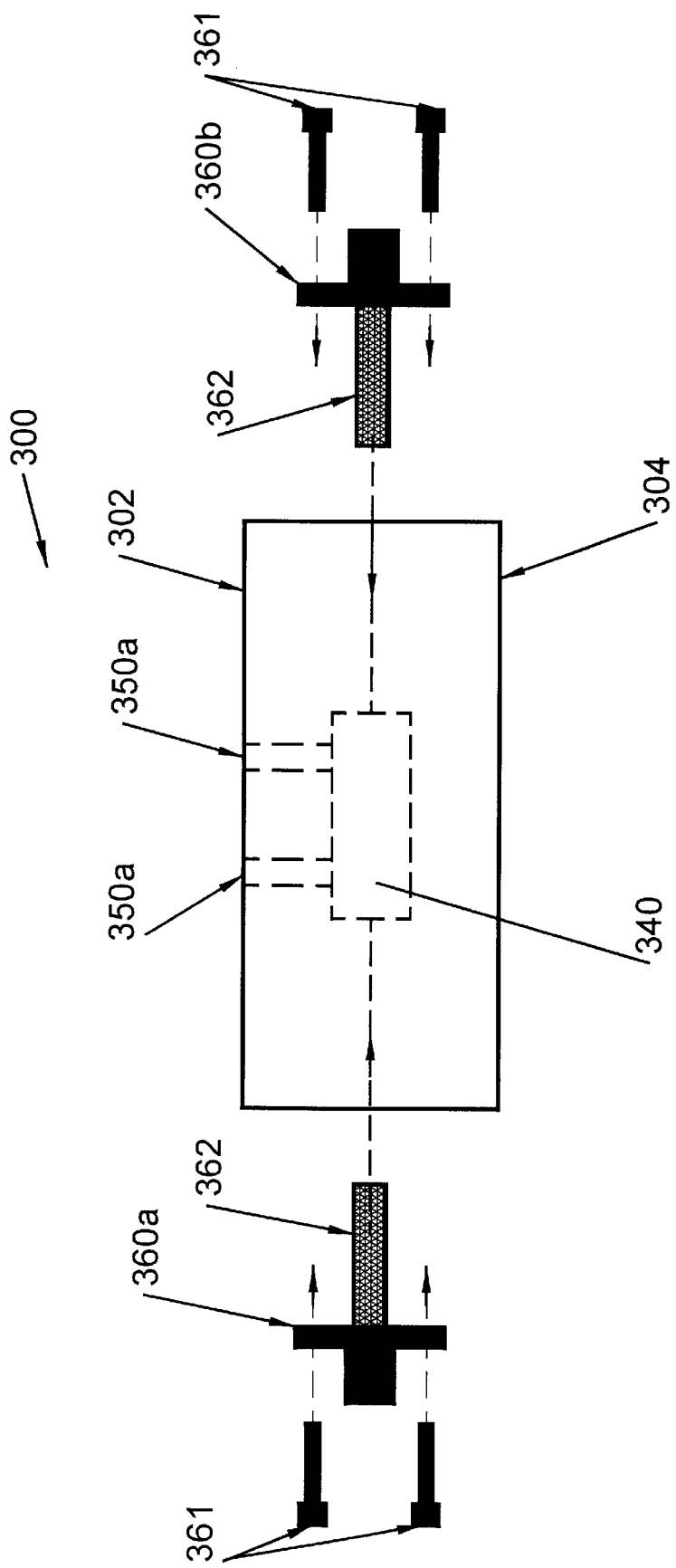

FIG. 3B illustrates an end view of the test fixture shown in FIG. 3A. As illustrated, test fixture 300 includes connectors 360a and 360b for communicating signals into and/or out of the test fixture 300. Connectors 360a and 360b are secured to top and bottom plates 302 and 304 via screws 361. Connectors 360a and 360b include center conductors 362 which are coupled to the bio-assay device 400 via transmission lines (not shown) formed between the top and bottom plates 302 and 304, respectively. In the preferred embodiment, connectors 360a and 360b are SMA connectors such as those manufactured by the SRI Connector Gage Company of Melbourne, Fla. (www.sriconnectorgage.com). In alternative embodiments, connectors 360a and 360b may consist of N, 3.5 mm, 2.9 mm, 2.4 mm or other connectors appropriate for the test frequency range. Fluid ports 350a are used to supply sample to the sample cavity 340.

Figure 3C:
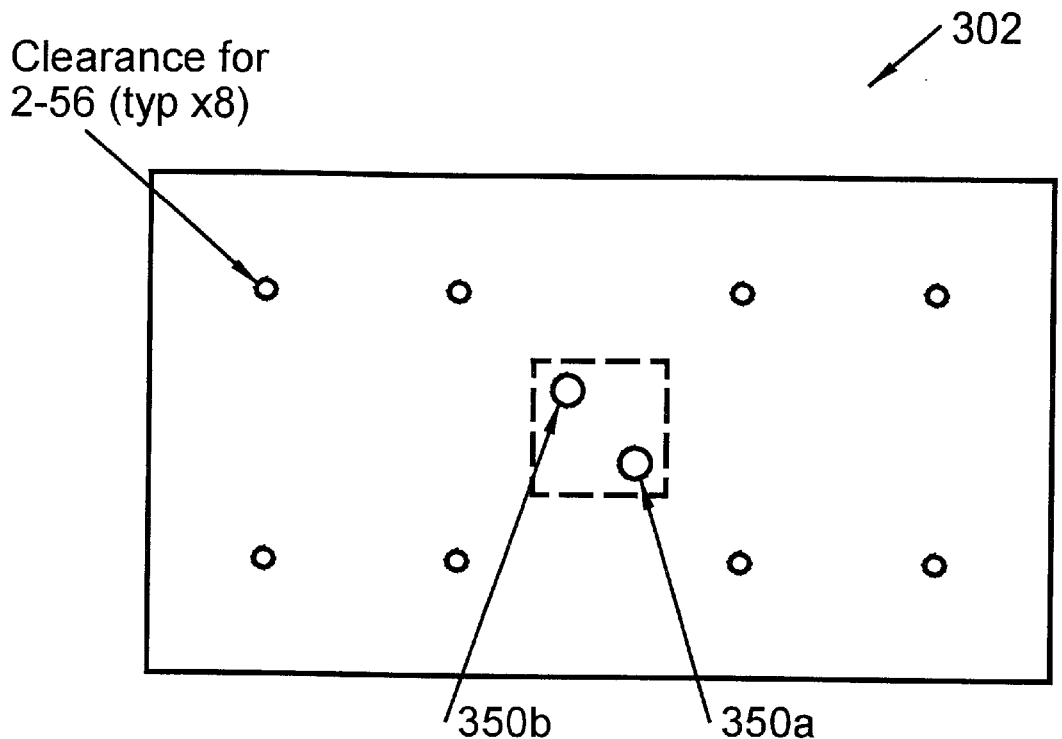
Figure 3D:
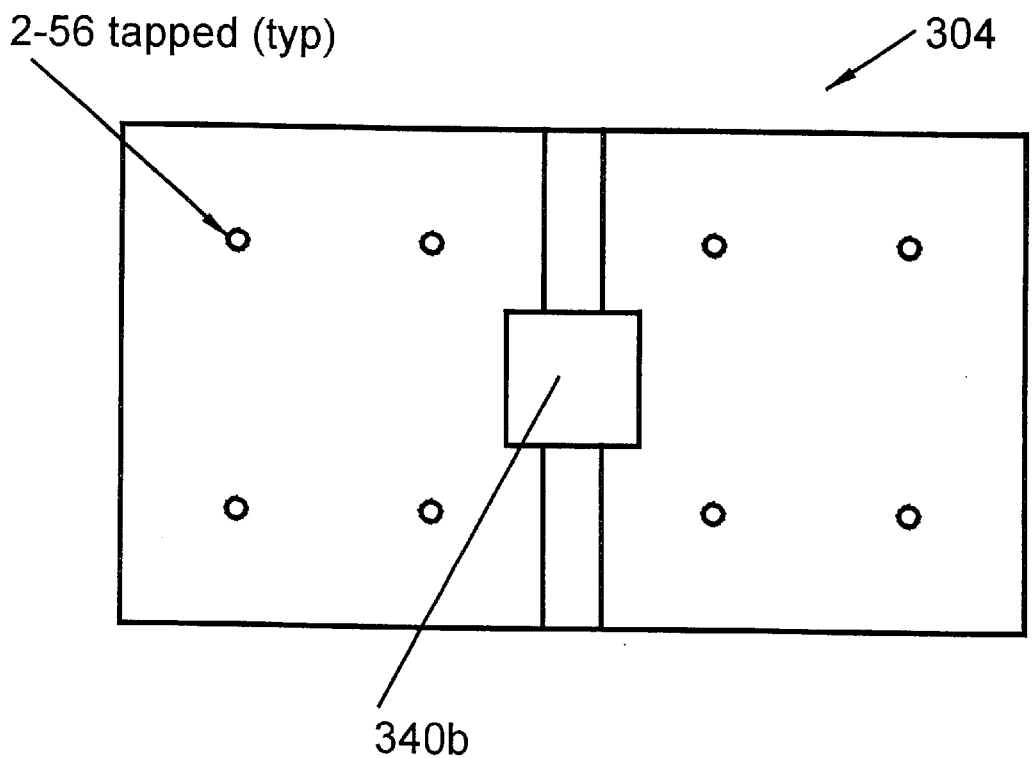
Figure 3E:
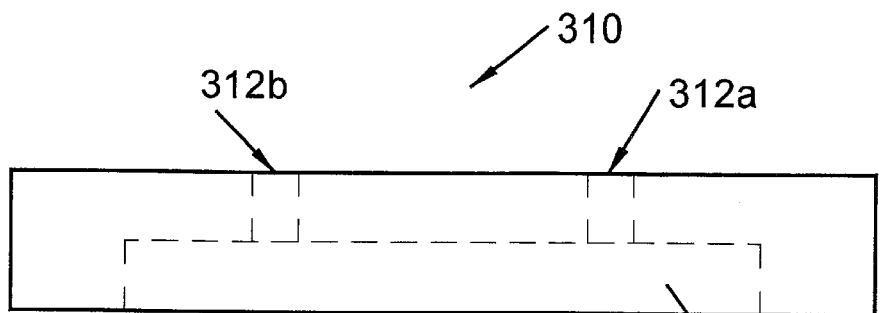
Figure 3F:
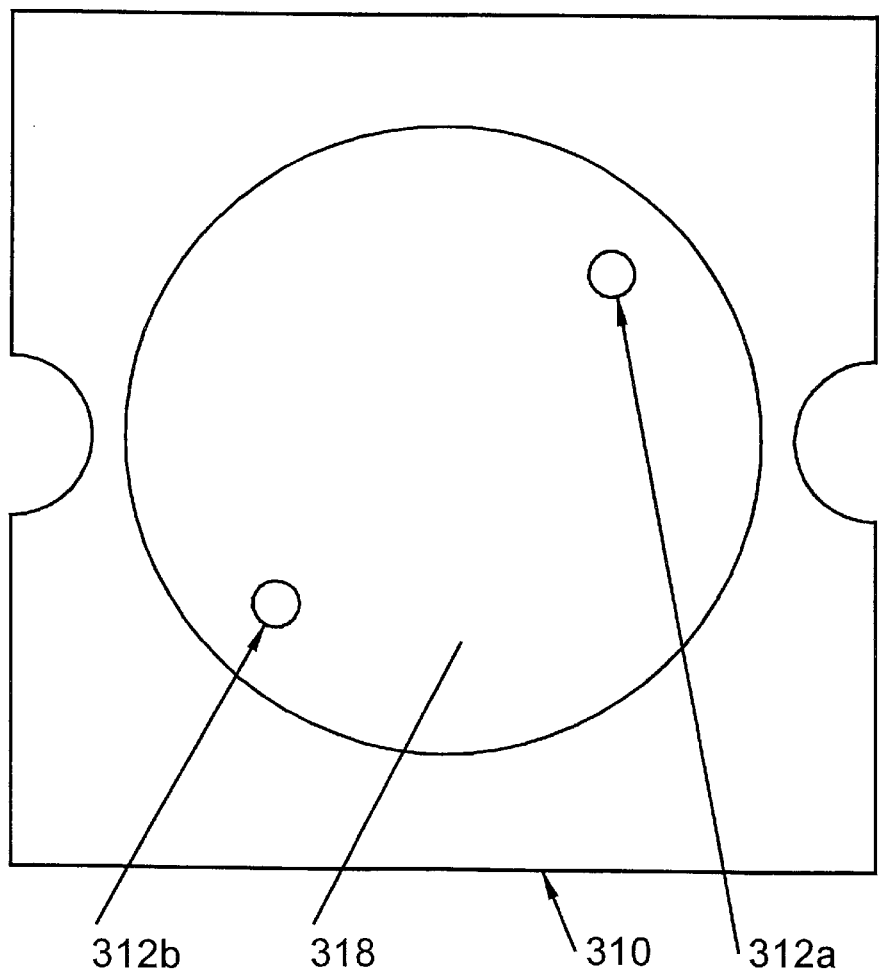

FIG. 3C illustrates a top view of top plate 302 showing ports 350a and 350b and top half of sample cavity 340a. In its preferred embodiment, top half of sample cavity 340a measures 0.4 cm×0.4 cm×0.080 cm. FIG. 3D illustrates a top view of bottom plate 304 showing the bottom half of sample cavity 340b, also measuring 0.40 cm×0.40 cm×0.080 cm in the preferred embodiment. FIGS. 3E and 3F illustrate side and bottom views respectively of reaction vessel 310. In its preferred embodiment, reaction vessel is composed of Lexan® and measures 0.4 cm×0.4 cm×0.070 cm. Ports 312a and 312b are 0.030 cm diameter. O-ring cavity 318 has an diameter of 0.240 cm.

Figure 3H:
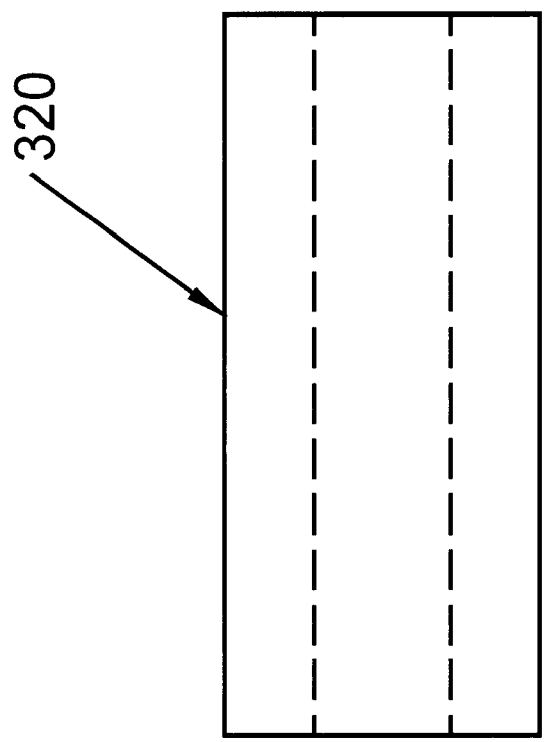
Figure 3G:
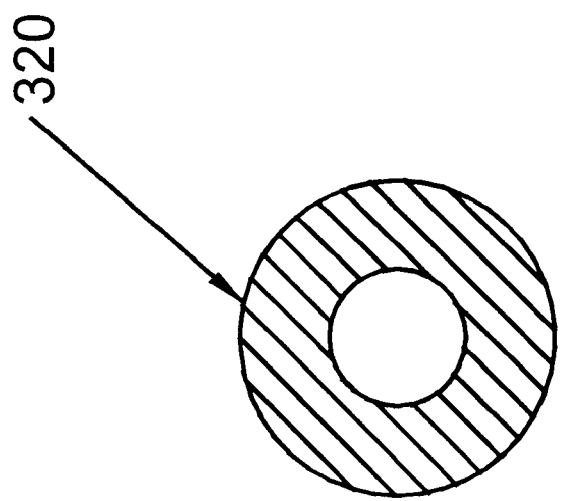
Figure 3I:
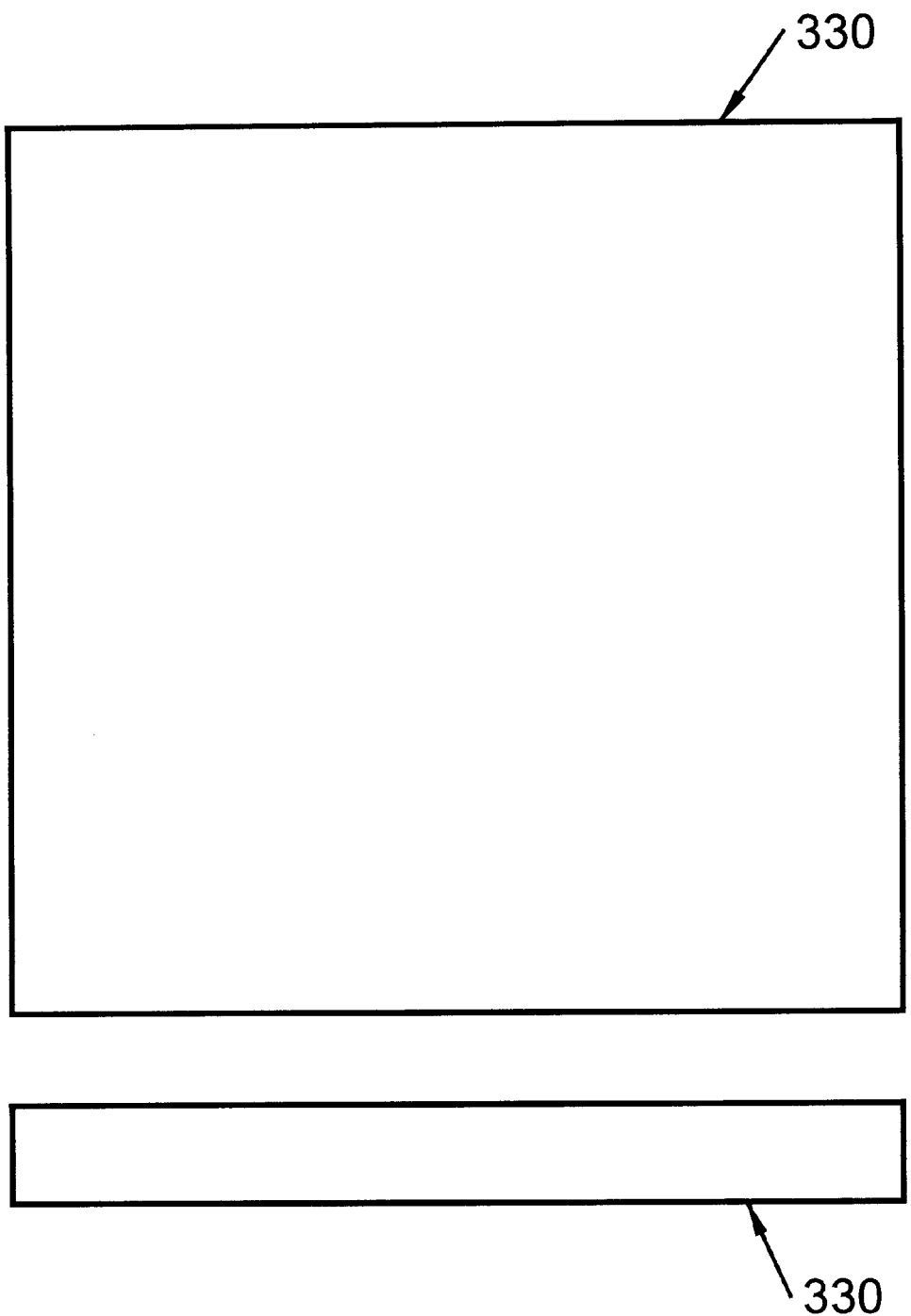

FIGS. 3G and 3H illustrate top and side views of O-ring 320, respectively. In the preferred embodiment, O-ring 320 is composed of an elastomer, such as Viton® and measures 0.100 cm×0.240 cm with an inner diameter of 0.030 cm. FIGS. 3I and 3J illustrate top and side views of bottom spacer 330. In the preferred embodiment, bottom spacer is composed of Lexan® or alumina and measures 0.4 cm×0.4 cm×0.025 cm.

C. Bio-Assay Device

The bio-assay device forms the bio-electrical interface of the present detection system. The device includes a signal path electromagnetically coupled to the MBR. One or more input/output ports are connected to the signal path to communicate the test signal. A single input/output port may be used, when for instance a reflection measurement, known in the art, is sought. Alternatively, separate input and output ports may be used when a through measurement, also known in the art, is sought alternatively or in addition to the reflection measurement.

The signal path is preferably formed along a direction which is non-orthogonal to the MBR. In one embodiment, the test signal propagates in parallel to a tangent on the surface on which the MBR is formed. In other embodiments, the test signal may propagate at an angle of ±1°, ±2°, ±3°, ±4°, ±5°, ±10°, ±15°, ±20°, ±30°, ±40°, ±45°, ±50°, ±60°, ±70°, ±80°, or ±85° relative to the MBR binding surface, or any ranges therebetween. In a first embodiment, the signal path consists of a transmission line in a two conductor structure and the direction of the signal path is defined by the Poynting vector as known in the art of electromagnetics. In a second embodiment, the transmission line may consist of a conductive region or layer which extends continuously along the bio-electrical interface region. In a third embodiment, the signal path maybe defined as the path having the least amount of signal loss along the bio-electrical interface over the desired frequency range of operation. In a fourth embodiment, the signal path maybe defined as having an a-c. conductivity of greater than 3 mhos/m, i.e., having a conductivity greater than that a saline solution, typically greater than 5 mhos/m, but ideally in the range of 100 to 1000 mhos/m and greater. As described above, the MBR may be either be in direct contact with or physically separated from but electromagnetically coupled to the signal path.

The signal path may be realized in a number of different architectures, such as a conductive wire, a transmission line, a conductive or dielectric waveguide structure, a resonant cavity, or any other transmission medium that will support the propagation of the test signal over the desired frequency range. At high test frequencies (frequencies above 10 MHz, for example) the signal path may be realized in microstrip, stripline, suspended substrate, slotline, coplanar waveguide, conductive or dielectric waveguide, or other high frequency signal path architectures such as those described in R. E. Collins *Foundations for Microwave Engineering,* McGraw-Hill Publishing Co., 1966; and S. March, *Microwave Transmission Lines and Their Physical Realizations,* Les Besser and Associates, Inc., 1986. The following examples are but a few of the possible signal path embodiments within the scope of the present invention.

Through Microstrip Transmission Line

Figure 4A:
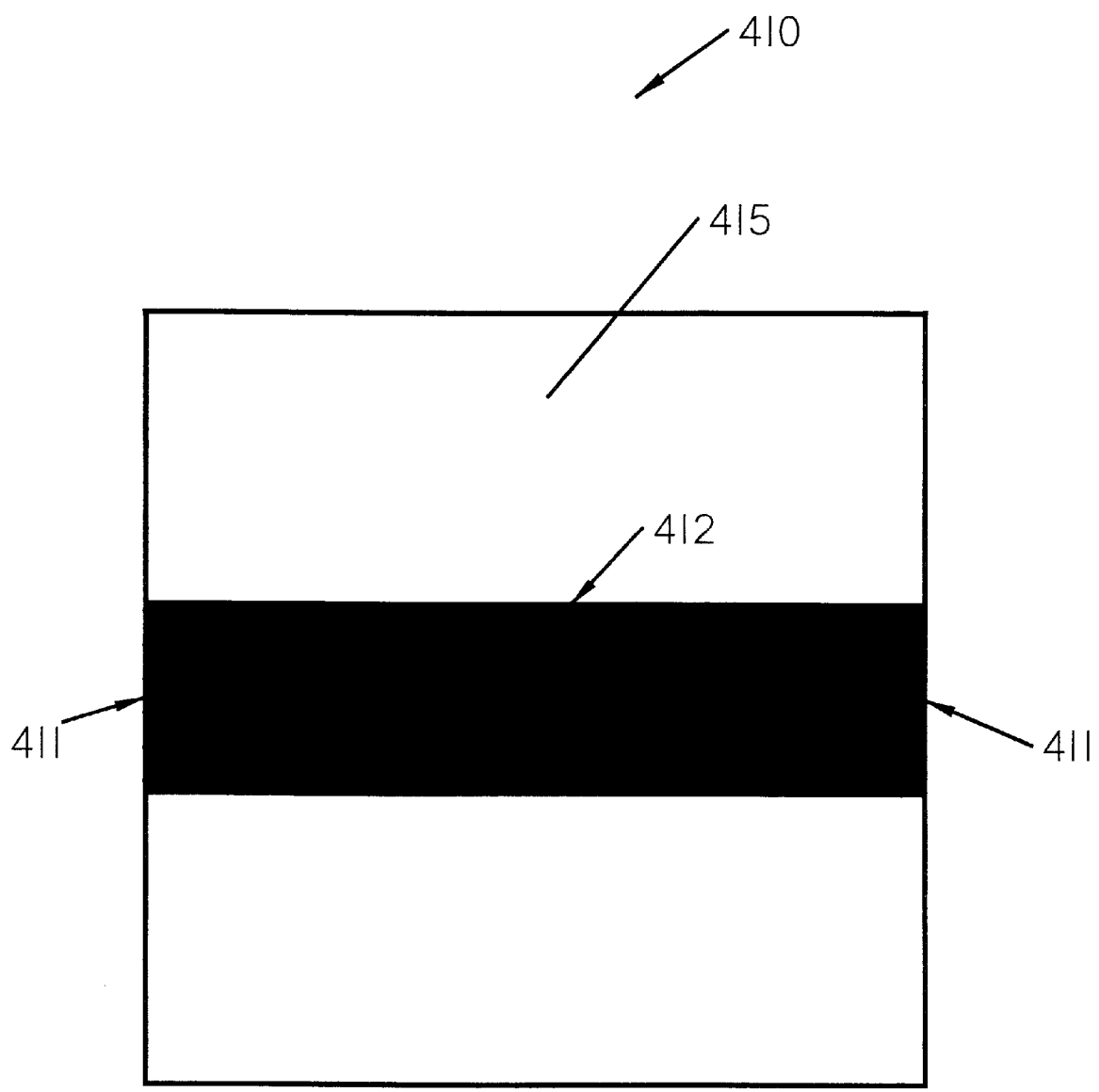
FIG. 4A illustrates a top view of a standard microstrip transmission line bio-assay for use with the test fixture of FIG. 3.

FIG. 4A illustrates a top view of a standard microstrip transmission line bio-assay 410 for use with the test fixture of FIG. 3A. As illustrated, the signal path consists of a transmission line 412 of width of 0.065 cm and length of 1.0 cm between the input/output ports 411. Bio-assay 410 is formed using standard photolithographic techniques and fabricated using sputtered gold transmission lines on a 0.55 mm thick quartz glass substrate 415 having a dielectric constant of approx. 3. Those of skill in the art will appreciate that other signal path architectures, conductive and substrate materials, and photolithographic techniques may be alternatively employed.

During a testing operation, a sample is applied over the transmission line 412 and a MBR is formed along the exposed surface of the transmission line 412. The MBR may be either in direct physical contact with the transmission line 412 or separated from but electromagnetically coupled to the line 412. In the embodiment in which the MBR is in direct contact with the transmission line, linker and/or matrix layers may be employed to facilitate binding thereto as further described in the incorporated patent application entitled: "Method and Apparatus for Detecting Molecular Binding Events," Ser. No. 09/243,194.

Next, a test signal is launched on to the transmission line 412 through, for example, an SMA type connector 360, shown in FIG. 3B. As the test signal propagates along the transmission line portions have a MBR attached or in close proximity thereto, the dielectric properties of the MBR modulate the test signal. The modulated test signal is then be recovered and used to detect and identify the molecular binding events occurring within the MBR.

Meandered Microstrip Transmission Line

Figure 4B:
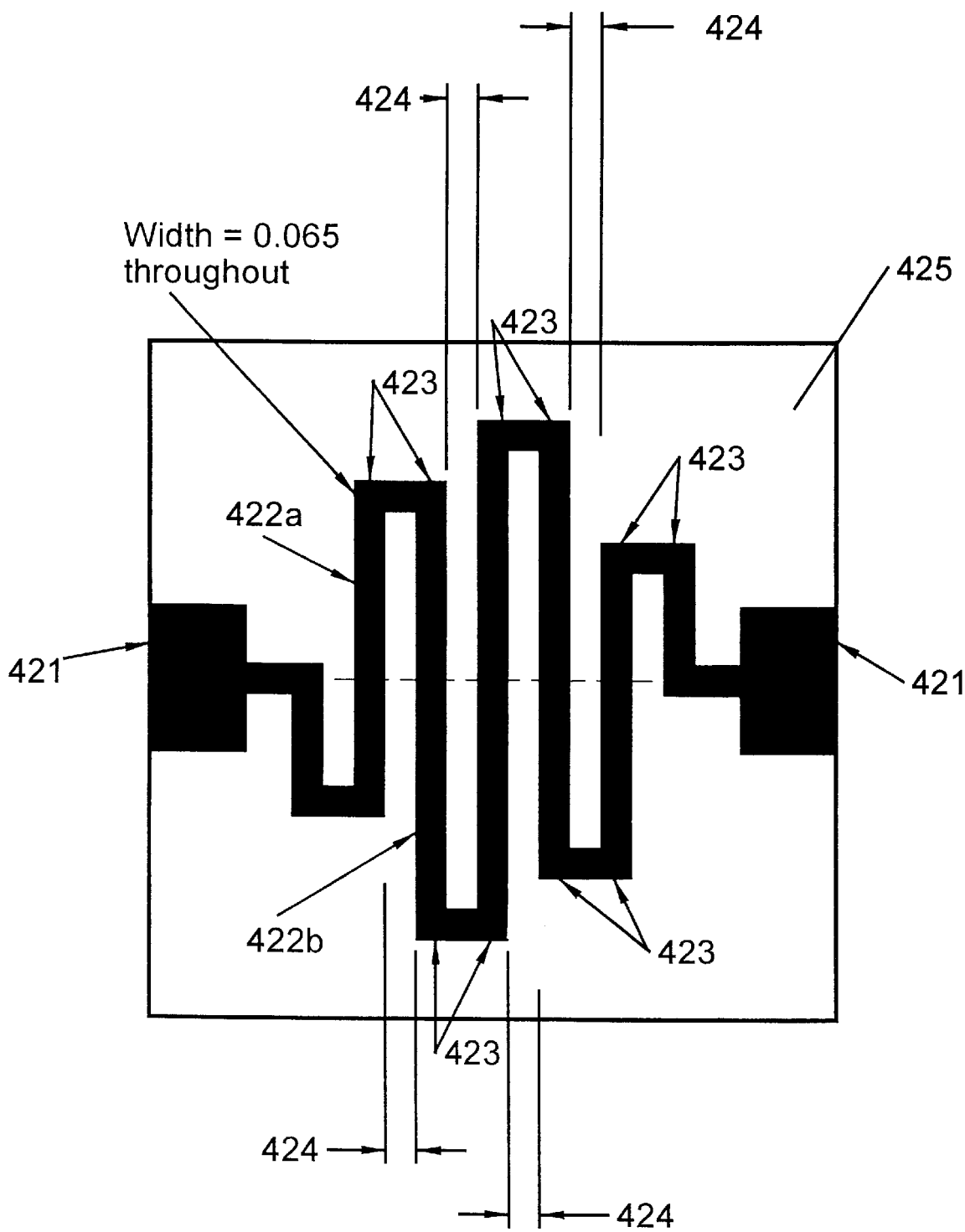
FIG. 4B illustrates a top view of a meandered transmission line bio-assay for use with the test fixture of FIG. 3.

FIG. 4B illustrates a top view of a meandered transmission line bio-assay 420 for use with the test fixture of FIG. 3A. Bio-assay 420 includes a meandered line coupled between an input/output ports 421. The meander line 422 is designed to increase the MBR surface area which provides greater measurement sensitivity, while adding minimal length and size to the detection structure.

In the illustrated embodiment, the meandered line 422 has a width of 0.065 cm and length of 1.0 cm between the input/output ports 422. Transmission line corners 423 may be mitered, 45° to minimize signal reflection and maximize signal transmission along the line 422. Spacing 424 is designed to minimize coupling between proximate line sections. In one embodiment, line spacing is 0.033 cm. In an alternative embodiment line spacing 424 is defined such that coupling between proximate line sections 422a, 422b is no more than −7 dB. Bio-assay 420 is formed using standard photolithographic techniques and fabricated using sputtered gold transmission lines on a 0.55 mm thick quartz glass substrate 425 having a dielectric constant of approx. 3. Those of skill in the art will appreciate that other signal path architectures, conductive and substrate materials, and photolithographic techniques may be alternatively employed.

During a testing operation, a sample is applied over the meandered line 422 and a MBR is formed along the exposed surface of the meandered line 422. The MBR may be either in direct physical contact with the meandered line 422 or separated from but electromagnetically coupled to the line 422. Linker and/or matrix layers may be used to facilitate binding to the meandered line 422.

Next, a test signal is launched on to the transmission line 422 through, for example, an SMA type connector 360, shown in FIG. 3B. As the test signal propagates along the transmission line portions have a MBR attached or in close proximity thereto, the dielectric properties of the MBR modulate the test signal. The modulated test signal is then be recovered and used to detect and identify the molecular binding events occurring within the MBR.

Numerous variations in the illustrated design may be realized to increase the detection sensitivity over a minimum detection area. For instance, when employed miters may be designed to provide an intentional impedance mismatch between line segments, thereby causing signal reflections between miters. When the effective signal length of the line segment approaches 180 degrees, the reflected signals will combine in phase with incoming signals, thereby a larger amplitude output signal at these frequencies. Higher output power permits greater measurement sensitivity and the length of the line segments can be tune to detect or more closely inspect responses occurring at specific frequencies.

Microstrip Ring Resonator

Figure 4C:
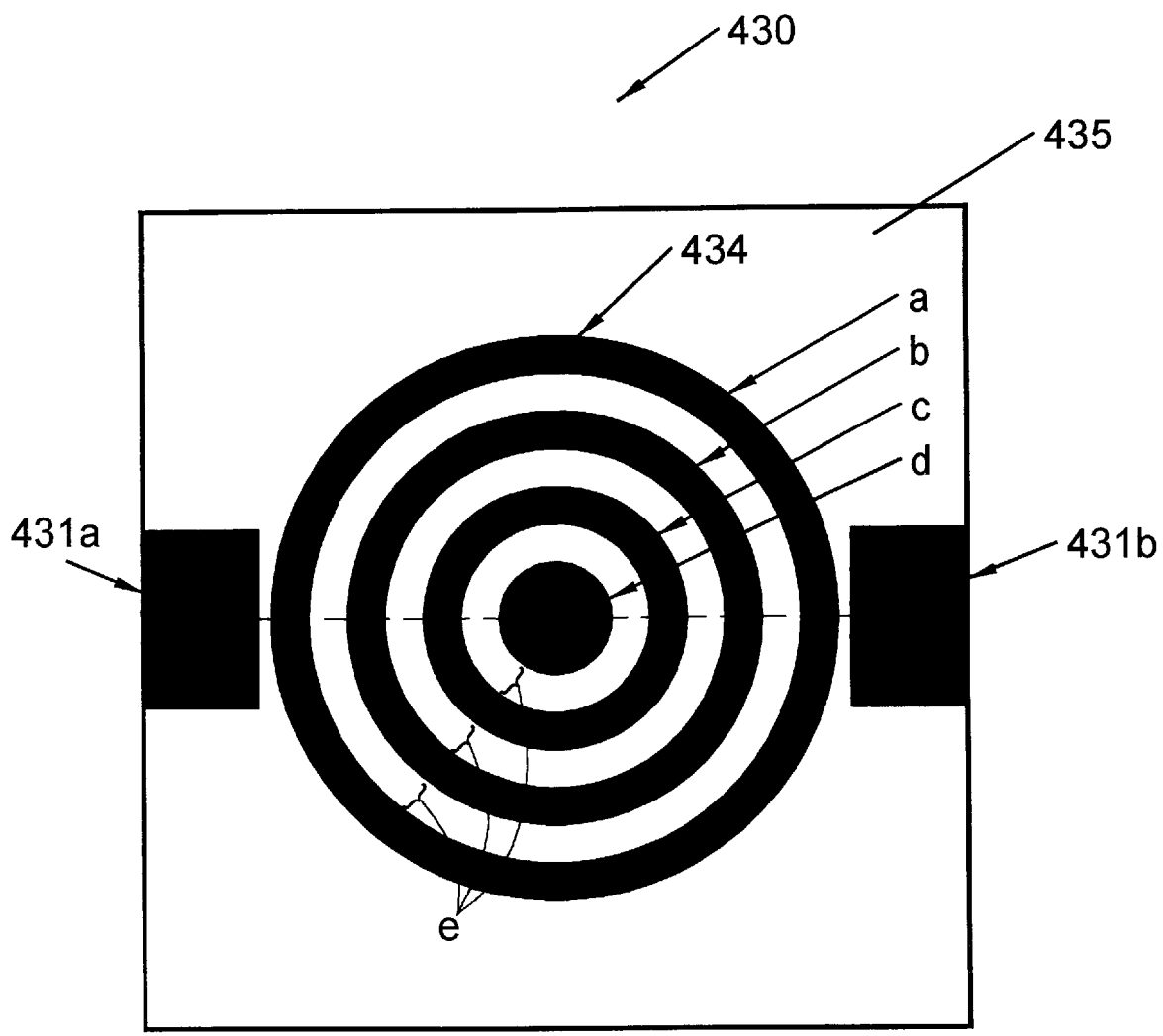
FIG. 4C illustrates a top view of a ring resonator bio-assay for use with the test fixture of FIG. 3.

FIG. 4C illustrates a top view of a ring resonator bio-assay 430 for use with the test fixture of FIG. 3A. The bio-assay 430 includes input/output ports 431a and 431b coupled to a ring( resonator 434. Ring resonator 434 includes three concentric rings 434 a–c and a solid circular ring 434d disposed therein. Each ring 434a–c has a width of 0.1 cm and is separated from proximate ring(s) by a spacing of 0.1 cm. The solid circular element 434d is 0.050 cm in radius and is disposed at the ring center. In alternative embodiments, spacing 434e and/or widths may vary from ring to ring. Bio-assay 430 is formed using standard photolithographic techniques and fabricated using sputtered gold transmission lines on a 0.55 mm thick quartz glass substrate 435 having a dielectric constant of approx. 3. Those of skill in the art will appreciate that other signal path architectures, conductive and substrate materials, and photolithographic techniques may be alternatively employed.

During normal operation without an applied sample, a test signal is injected into the port 431a through, for example, an SMA connector 360 as shown in FIG. 3B. Via electromagnetic coupling, a portion of the test signal propagates through the ring resonator 434 and to the output port 431b. An impedance mismatch occurs at this interface 431b, reflecting a portion of the signal back toward the source interface 431a. The remaining portion of the signal propagates out of the resonant circuit along the input line segment and to the test set. At the source interface 431a, a second impedance mismatch occurs and reflecting a portion of the reflected signal again toward the resonator output 431. The remaining portion of the signal is propagated out of the resonant circuit along the output line segment toward the test set input. The signal continues to "ping-pong" between the interfaces 431a and 431b until the signal is dissipated or transmitted to the source or test set. The magnitude of the reflected wave depends in part on the magnitude of the impedance mismatch at the interfaces 431a and 431b. The larger the impedance mismatches, the larger the reflected signal.

At one or more frequencies, the effective signal path between interfaces 431a and 431b approaches a 180° phase shift (or a multiple thereof). When this occurs, the reflected signal will reach input interface 431a having a phase substantially equal to the phase of the incoming signal. In this instance, the incoming signal and the reflected signal will recombine in-phase, thereby producing a stronger signal. When the stronger signal reaches the output interface 431b, a larger magnitude signal (compared to the non-combined signal) will exit from the output interface 431b to the test set. Thus, the resonator 434 will output a larger magnitude signal near frequencies in which the resonator 434 has an effective signal length near 180° or a multiple thereof. This difference in output signal strength can be monitored and detected using the measurement systems described herein.

When the sample is applied over the resonator 430, a MBR is formed along the exposed portion of rings 434a–d. The MBR may either be in direct physical contact with the rings or separated from but electromagnetically coupled to the rings 434a–d. Linker and/or matrix layers may be employed to facilitate binding to the resonator rings 434a–d and/or input and output interfaces 431a and 431b.

Next, a test signal is injected into the input port 431a as above. The test signal couples between rings of the resonator 434 as before, except that the dielectric properties of the MBR operates to change the frequency(s) at which the resonator 434 approaches 180°. Further, because the dielectric properties of each different MBR are distinct, each MBR will produce a different "frequency marker", i.e., the frequency at which the resonator approaches a 180° phase shift and produces a larger output signal. In this manner, samples containing different molecular structures will exhibit different frequency markers, which can be used to detect their presence in an unknown solution. In addition, molecular structures within a particular class, alpha-helices, beta-sheets and other structural motifs in proteins may exhibit "related" frequency markers, e.g., frequency markers within close proximity to each other or frequency markers which occur within a predictable pattern.

Those of skill in the art of Microwave engineering will understand that other resonant structures are also possible. For instance, the resonator 434 may alternatively consist of a transmission line segment connected between the input and output interfaces 431a and 431b. In this embodiment, the transmission line segment will have the appropriate impedance relative to the input and output ports to provide the desired input and output impedance mismatch and the appropriate length to provide the 180° phase shift in presence of the sample. Other resonant configurations such as a proximately placed dielectric puck as well as others may be used with minor modifications to detect the presence or absence of particular molecular structures.

A, Microstrip Capacitive Gap

Figure 4D:
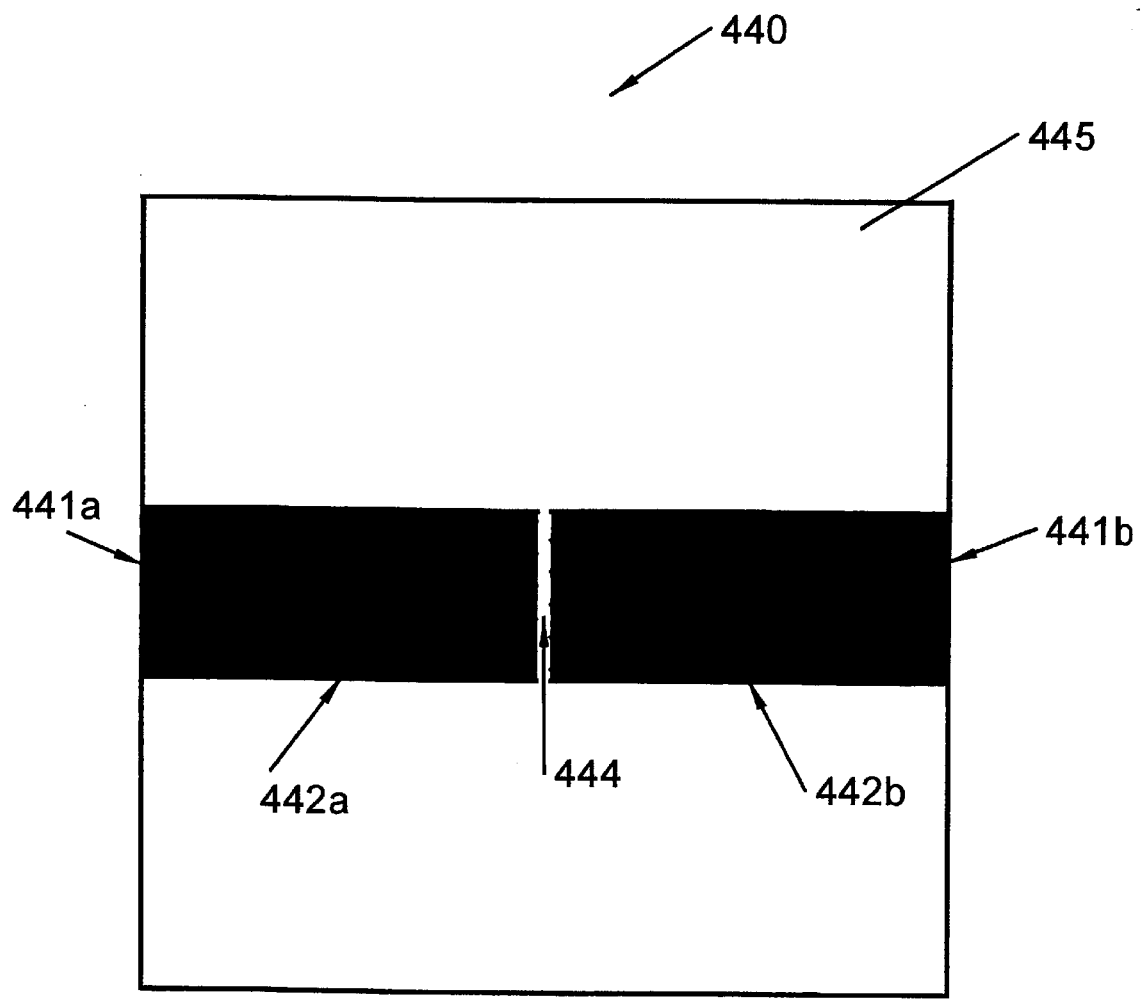
FIG. 4D illustrates a top view of a capacitive gap bio-assay for use with the test fixture of FIG. 3.

FIG. 4D illustrates a top view of a capacitive gap bio-assay 440 for use with the test fixture of FIG. 3A. Bio-assay 440 includes an input port 441a coupled to an input line segment 442a and an output port 441b coupled to an output line segment 442b. Disposed between the input and output line segments 442a and 442b is a gap 444 where the sample is deposited during testing. In the illustrated embodiment, input and output line segments 442a and 442b are each 0.495 mm long and 0.250 mm wide. Capacitive gap 444 measures 0.010 mm×0.250 mm. Bio-assay 440 is formed using standard photolithographic techniques and fabricated using sputtered gold transmission lines on a 0.55 mm thick quartz glass substrate 445 having a dielectric constant of approx. 3. Those of skill in the art will appreciate that other signal path architectures, conductive and substrate materials, and photolithographic techniques may be alternatively employed.

During normal operation without an applied sample, a test signal is injected into the port 441a through, for example, an SMA connector 360 as shown in FIG. 3B. Via electromagnetic coupling, a portion of the test signal's electromagnetic field propagates across the capacitive gap 444 between the input and output line segments 442a and 442b. The capacitive gap 44 prevents the transmission of D.C. voltage and current from passing between the input and outputs. The test signal is then recovered at the output port 441b for processing. The width and separation of the gap 444, impedances of input and output line segments 442a and 442b, the dielectric constant of the substrate 445, and the frequency of operation will influence the amount of signal power transferred between the input and output ports 441a and 441b. The bio-assay capacitive gap circuit 440 will exhibit a signal response which varies over a test frequency range.

When the sample is applied over the gap 444, a MBR is formed along the edges of input and output line segments 442a and 442b. The MBR may either be in direct physical contact with the line segment edges 442a and 442b, or separated from but electromagnetically coupled thereto. Linker and/or matrix layers may be used on the line segments 442a and 442b to promote molecular binding thereto.

The formation of the MBR on gap edges effects the signal's transmissivity from the input port 441a to the output port 441b. Specifically, the MBR creates a gap circuit, the response of which varies over the test frequency range. As described above, each distinct MBR will exhibit a different dielectric property which serves to create a distinct frequency response or "signature." The frequency signature of a known molecular sample can stored and later used to identify the molecular structure in an unknown solution. Molecular structures within the same class may exhibit a similar frequency pattern over a common test frequency range. In this case, the tester is able to identify the class of the unknown molecular structure if the identity of the molecular structure itself is known.

The capacitive configuration may be used as a single detection element or in combination with one or more of the detection elements listed herein to enhance, tune, or detune the frequency response at one or more frequencies.

Dielectric Signal Path

Figure 4E:
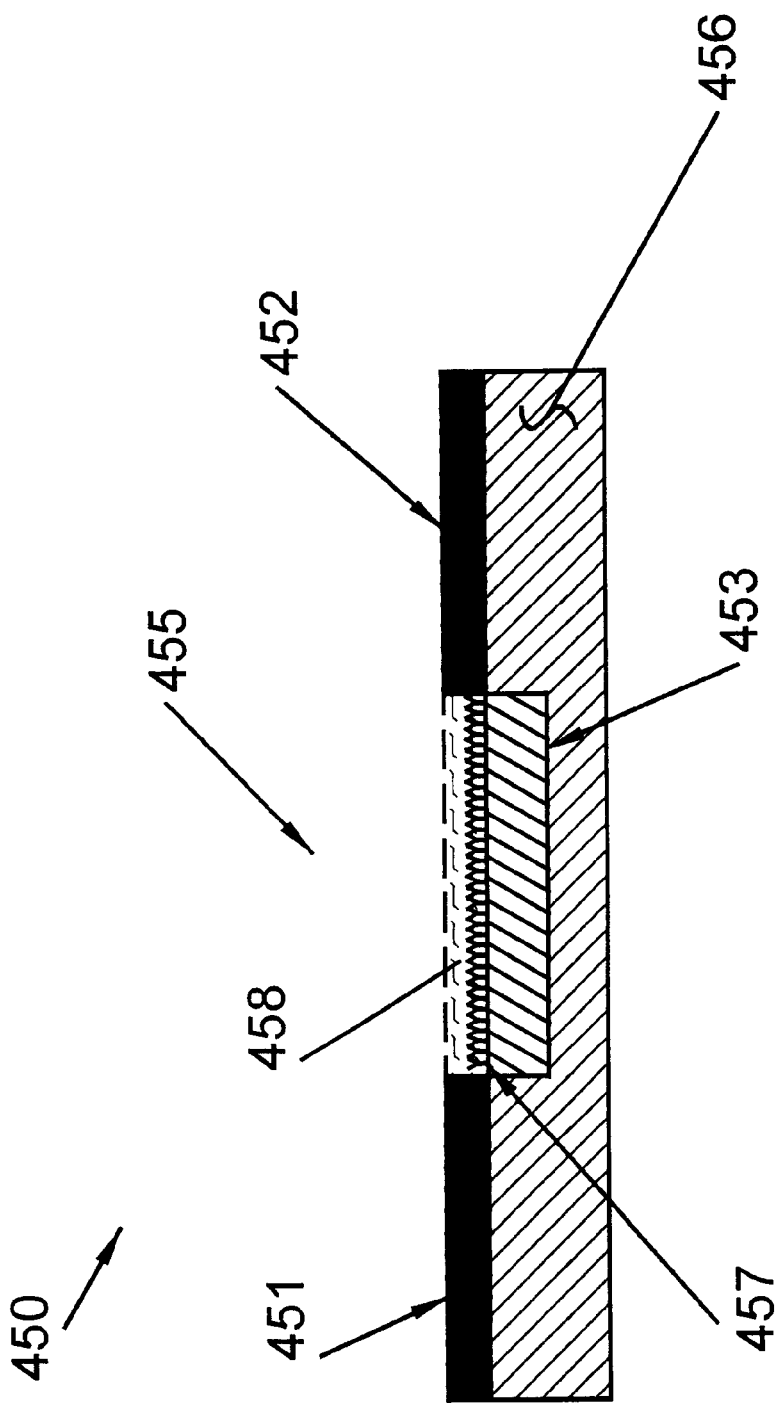
FIG. 4E illustrates a side view of a dielectric signal path bio-assay for use with the test fixture of FIG. 3.

FIG. 4E illustrates a side view of a dielectric signal path bio-assay 450 having for use with the test fixture of FIG. 3. Bio-assay 450 includes an input line segment 451, an output line segment 452 formed on a dielectric substrate 456, and a dielectric region 455 disposed between the input and output line segments 451 and 452. The bottom surface of dielectric region 455 is formed by insulating substrate 453 which is treated to promote molecular binding thereto. The insulating substrate 453 may consist of the same or different material as the dielectric substrate 456. Further, the insulating substrate 453 may include of linker and/or matrix layers, further described in the commonly owned, copending U.S. patent application entitled "Method and Apparatus for Detecting Molecular Binding Events," Ser. No. 09/243,194, filed Feb. 2, 1999 incorporated herein by reference. In the exemplary embodiment of FIG. 4E, the bio-assay 450 is fabricated using standard microstrip photolithographic techniques on a dielectric substrate 456 of 0.55 mm quartz glass substrate having a dielectric constant of approximately 3. The dielectric region 455 is 100 Angstroms deep and extends 2.5 um between the input and output line segments 451 and 452.

When a sample 456 is applied over the dielectric region 455, a longitudinal MBR 457 is formed along the surface of the insulating substrate 453. The formed MBR serves as a signal path for the test signal. As described above, the MBR 457 exhibits a dielectric property which modulates the test signal and each MBR 457 will exhibit a different dielectric property which will in turn modulate the test signal differently. The modulated'signals or "signatures" are largely unique and can be associated with samples having known molecular binding events. These stored signals can later be used to identify the molecular structure in an unknown solution. Molecular structures within the same class may exhibit a similar frequency pattern over a common test frequency range. In this case, the tester is able to identify the class of the unknown molecular structure if the identity of the molecular structure is known.

IV. Array Test System and Bio-assay

A multitude of bio-assay devices, some examples of which are described in FIGS. 4A–E, may be implemented in an N×M array test structure to perform high through-put analysis. In this configuration, N×M different binding events may be detected, for instance to enable fast characterization of oligonucleotides such as single nucleotide polymorphism, individual genes, and longer sequences of the nucleic acides. The number of inputs may be the same as the number of outputs in which case M=N, or the number of inputs and outputs may differ.

The array may be fabricated using conventional photolithographic processing to form one or more biosensors on a substrate, such as the 0.5 mm$^2$ devices described above. Alternatively, the array may be fabricated using semiconductor processing techniques, such as Silicon Dioxide ($SiO_2$) or Gallium Arsenide (GaAs) processing. In this embodiment, the array in wafer form may include $10^1$, $10^2$, $10^3$, $10^4$, $10^5$, $10^6$, $10^7$, $10^8$, $10^9$, $10^{10}$ bio-assay devices/mm or range anywhere therebetween.

A. Test System

Figure 5:
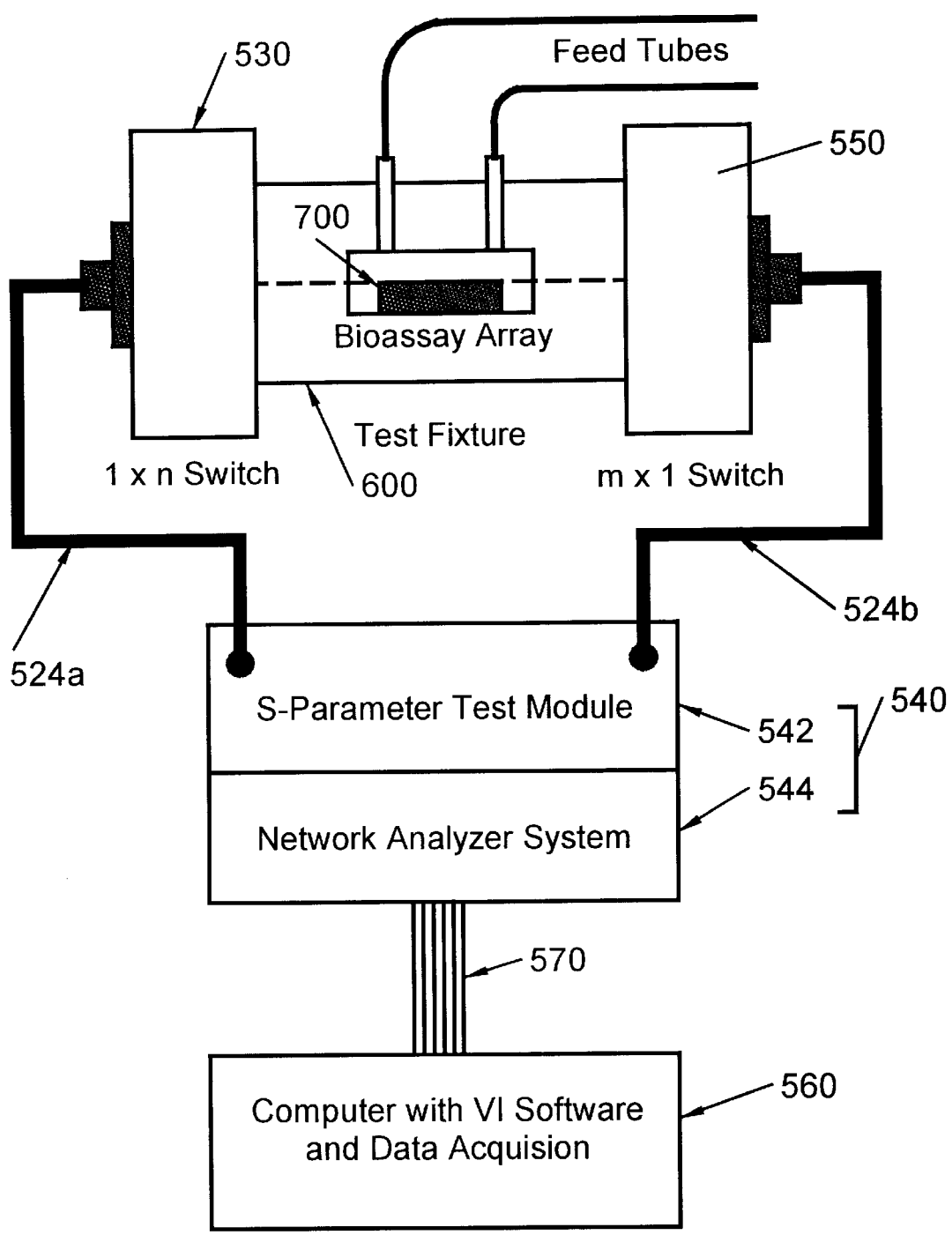
FIG. 5 illustrates one possible embodiment of an N×M array test system in accordance with the present invention.

FIG. 5 illustrates one possible embodiment of an N×M array test system 500 in accordance with the present invention. The test system includes a test fixture 600 further described below, a 1×N input switch 530, a measurement system 540, a M×1 output switch 550, and a computer 560. Measurement system 540 communicates test signals to the test fixture 600 via input test cable 524a and 1×N input switch 530. The test signal is subsequently received from the test fixture via M×1 output switch 550 and output test cable 524b. Computer 560 controls 1×N input switch 530, measurement system 540, and M×1 output switch 550 via a control bus 550.

In one embodiment, measurement system 540 may consist of the previous described measurement system 240 (S-parameter module 542 and network analyzer system 544) or any of the alternative embodiments described herein. Similarly, input and output test cables 524a and 524b, control bus 570, and computer 560 may consist of those previously described and/or their alternatives.

The 1×N input switch 530 routes the test signal from the input test cable 524a to one of the N test fixture signal inputs. The M×1 output switch 550 routes the test signal from one of the M test fixture outputs to the output test cable. Input and output switches 530 and 550 may consist of any switching or multiplexing means which will support the propagation of the desired test signal. For instance, input and output switches 530 and 550 may consist of low frequency switches (DC to 2 GHz), such as those manufactured by Amplifonix, Inc. of Philadelphia, Pa. (www.amplifonix.com). Switches for use at higher frequencies (2–18 GHz), such as those manufactured by the General Microwave Corporation of Amityville, N.Y. (www.generalmicrowave.com) may alternatively be employed. Connection between bio-assay device and input and output switches 530 and 550 may be made using insulated cables, wire bonds, or other conventional interconnection means appropriate for the test frequency of operation.

In an alternative embodiment, input and output switches 530 and 550 and the bio-assay array form a monolithic integrated circuit. For instance, when the bio-assay array is fabricated using GaAs semiconductor processing techniques, input and output switches 530 and 550 may consist of integrally formed PIN diodes which are coupled to the bio-assay array. Further alternatively, input and output switches 530 and 550 may form an integrated assembly in which the input and output switches 530 and 550 are discrete components which are connected (via wire or ribbon bonds) to the bio-assay array. Both alternative embodiments provide advantages in that the interconnecting structures are miniaturized or eliminated, thereby reducing or eliminating the signal loss associated therewith.

As explained, the bio-assay array 700 may be fabricated in wafer form using semiconductor processing techniques. In this embodiment, the array test system 500 may consist of a wafer probe test station, such as those manufactured by Cascade Microtech, Inc. of Beaverton, Oreg. (www.cascademicrotech.com) which includes or is coupled to the aforementioned input and output switches 530 and 550, and computer 560. The wafer probe station utilizes one or more probe cards, each of which is capable of providing a large number of low loss, low VSWR signal interconnections to the bio-assay array.

The probe card(s) may be used to provide N and/or M signal interconnections to the remotely located input and/or output switches 530 and 550, respectively. Alternatively, input and/or output switches 530 and 550 may be monolithically fabricated with the bio-assay array, in which case the probe card(s) provides a single input and/output signal transition to the measurement system 540. In this latter embodiment, the probe card(s) includes probes for providing switch control voltages to the monolithically formed switches.

Alternatively or in addition, measurement system 540 may include a Time Domain Reflectometer (TDR) system, such as those optionally available with the aforementioned network analyzers or described in the incorporated patent application entitled: "Method and Apparatus for Detecting Molecular Binding Events," Ser. No. 09/243,194.

B. Array Test Fixture

Figure 6A:
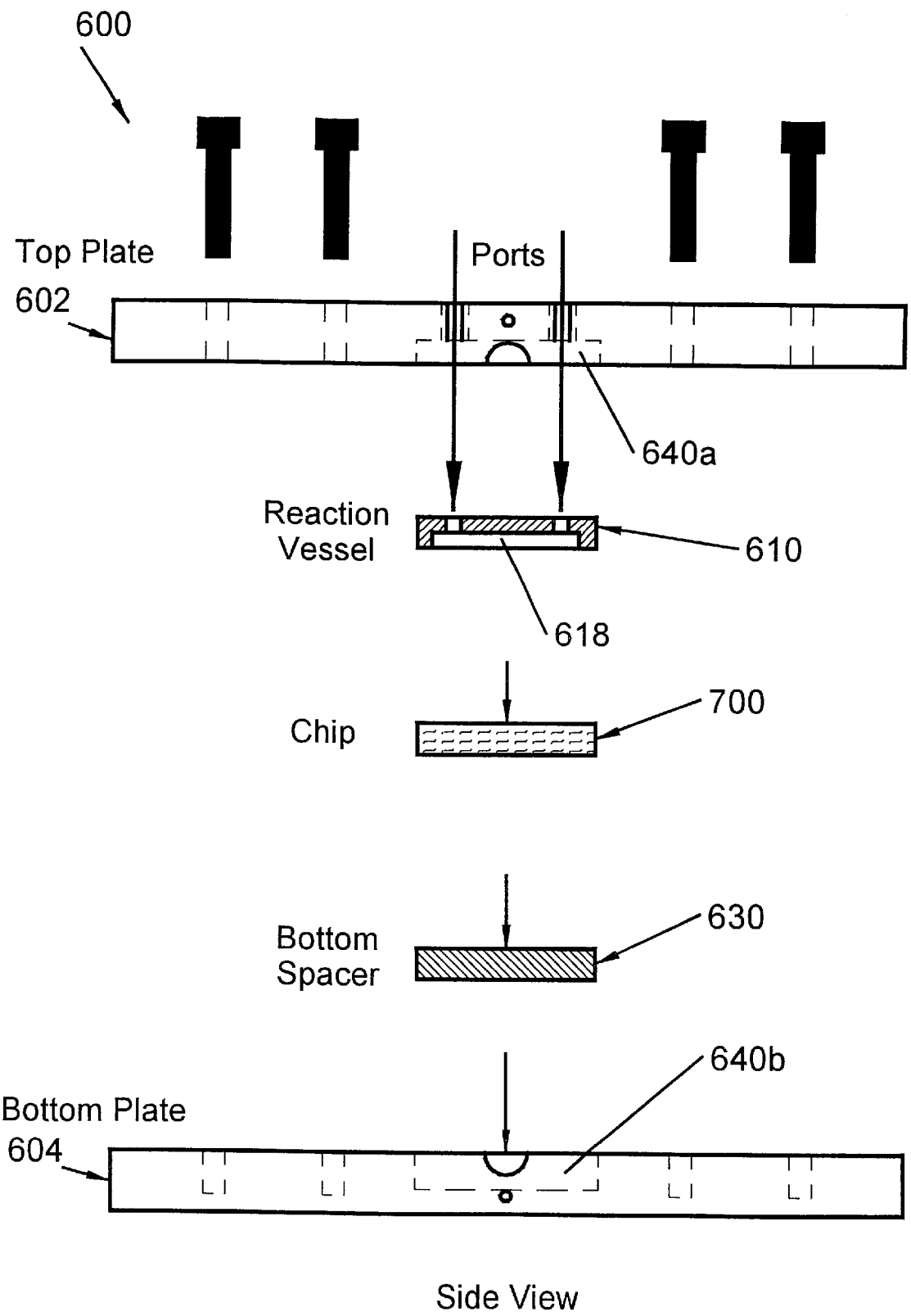
FIGS. 6A–B illustrate various views of an N×M array test fixture in accordance with the present invention.

FIG. 6A illustrates a side view of one possible embodiment of the N×M array test fixture 600 in accordance with the present invention. Similar in construction to the single path test fixture 300 shown in FIG. 3, test fixture 600 includes a top plate 602, bottom plate 604, and a sample cavity 640 (having top and bottom recesses 640a and 640b, respectively) which holds the aforementioned reaction vessel 610, bio-assay device 700 (further described in FIG. 7 below), and bottom spacer 630 elements. In the illustrated embodiment, the supplied sample is contained on the top surface of the bio-assay device in recess 618 of the reaction vessel 610. In the N×M array test fixture embodiment, the dimensions of sample cavity 640 and correspondingly reaction vessel 610 and bottom spacer 630 are designed to accommodate the bio-assay device 700 which may be larger or smaller than the bio-assay device 300 shown in FIG. 3. Each array element includes a small, monolithically deposited structure to form a recessed area over the signal path in order to hold a portion of the applied sample in electromagnetic communication with the signal path of each array element. In another embodiment, MEMS (micro-electronic machining systems) technology may be used to fabricate the sample cavity at the bio-assay device level.

Figure 6B:
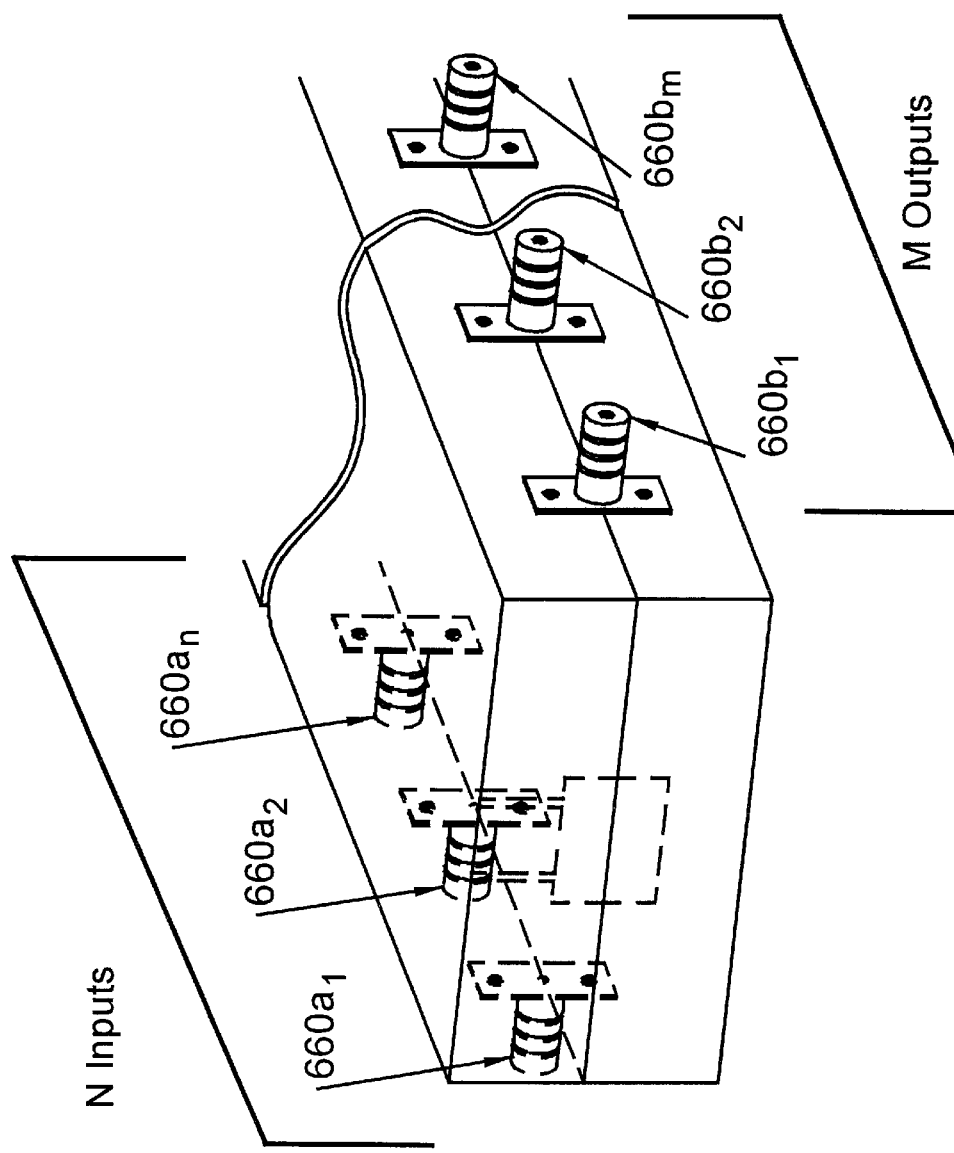

FIG. 6B illustrates an end view of the N×M array test fixture 600. Test fixture 600 includes N input connectors $660a_1$ to $660a_n$ and M output connectors $660b_1$ to $660b_m$. Test fixture 600 also includes N input transmission lines (not shown) which provide a signal transition between the fixture's N connectors $660a_1$ to $660a_n$ and the bio-assay's N inputs. Test fixture 600 further includes M output transmission lines (not shown) which transition between the bio-assay's M outputs and the fixture's M output connectors $660b_1$ to $660b_m$. The input and output transmission lines may be realized as insulated conductive wires, microstrip, stripline, coplanar waveguide transmission lines deposited on a dielectric substrate, or other conventionally known signal path architectures. The choice of the transmission line's architecture will be influenced by the test frequency band and the bio-assay device's input and output port density.

C. Bio-assay Array

Any or all of the structures shown in FIGS. 4A–4E can be used to form a bio-assay array in accordance with the present invention. The array may be fabricated on a discrete piece of dielectric substrate or in wafer form using semiconductor processing techniques. The array may include two or more of the above-mentioned structures on a single device, and coupled to diagnostic apparati via any of the standard switching techniques. Further active elements such as transistors may also be used as array elements, as will be further described below.

One, two, and three dimensional addressing may be used, with any number of addresses on the device itself. Each address may be designed to act as a logic gate in which a binary decision is made regarding binding or some other change in the MBR; to make decisions about three or more states, such as the shift in frequencies in a band limited system of resonators; or to measure a continuum of properties such as voltage, phase, frequency, or any of the other parameters as discussed above.

Figure 7A:
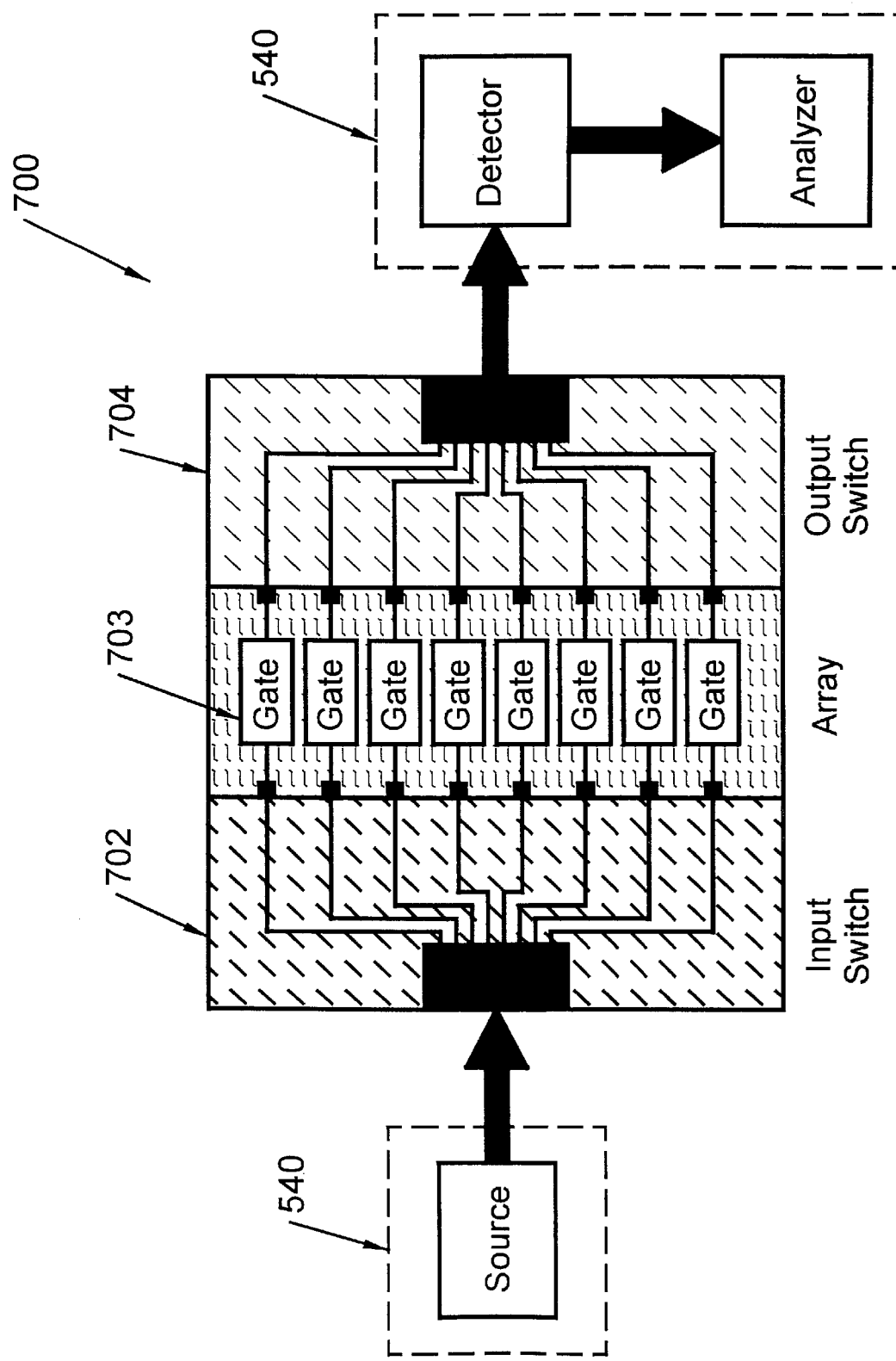
FIG. 7A illustrates one embodiment of a bio-assay array in accordance with the present invention.

FIG. 7A illustrates one embodiment of an integrated bio-assay array 700 in accordance with the present invention. The integrated array 700 is supplied with a test signal via the signal source of measurement system 540. The array 700 includes an integrated 1×N input switch 702a and M×1 output switch 704 which are monolithically formed during the semiconductor fabrication process. The number of inputs may be the same as the number of outputs in which case M=N, the number of inputs and outputs may differ.

The 1×N input switch 702 routes the incoming test signal to the desired array element within array 703. The MBR in the array element $703_j$ modulates the test signal according to the dielectric properties of the molecular binding events which make up the MBR. An M×1 output switch 704 routes the modulated test signal to a detector of the measurement system 540. An analyzer of the measurement system 540 compares the input and modulated test signals to determine the measured signal response. While each array element $703_j$ is illustrated as a two-port device, those of skilled in the art will appreciate that one-port or multiple port array elements may be used alternatively.

As explained above, the array 703 and the input and output switches 702 and 704 may be fabricated either as discrete components or in wafer form and integrated in varying degrees depending upon the application. In the illustrated embodiment, the array 700 and input and output switches are-monolithically formed on a semiconductor wafer. In another embodiment, the input and output switches 702 and 704 are monolithically formed separately from the array 703 and connected via wire or ribbon bonds. In a further embodiment, input and output switches 702 and 704 and array 703 are each discrete units. Those skilled in the art will appreciate that other arrangements are also possible.

Figure 7B:
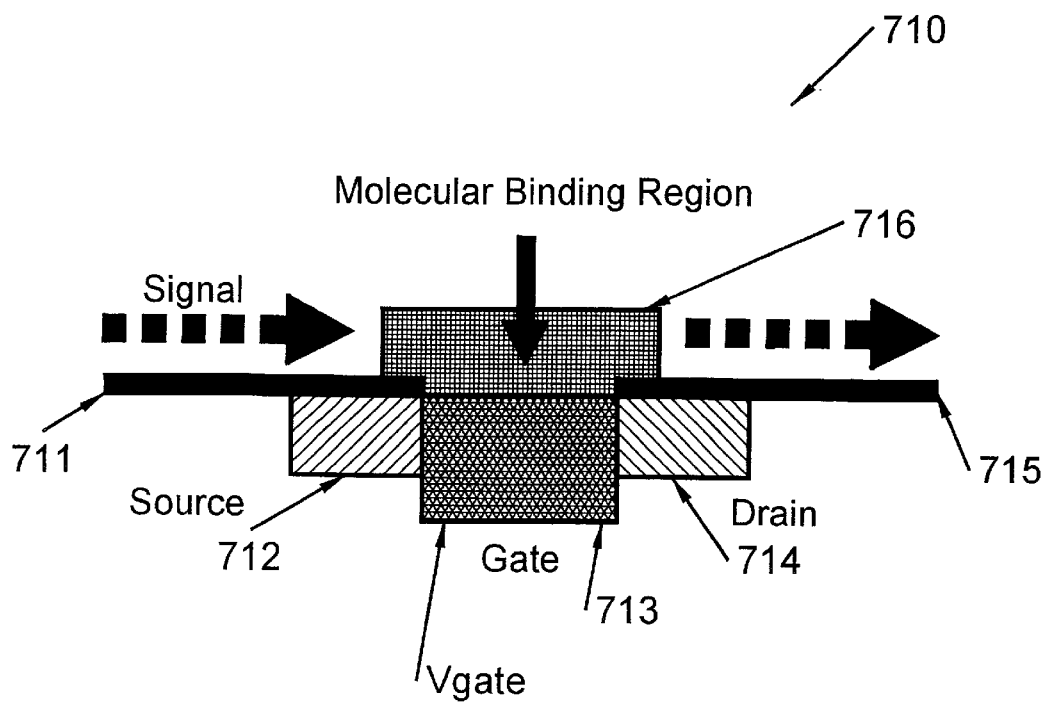
FIG. 7B illustrates one embodiment of an array element in accordance with the present invention comprising a series-connected, electronically switched Field Effect Transistor.

FIG. 7B illustrates one embodiment of an array element, shown as a series connected, electronically switched Field Effect Transistor (FET) 710. FET 710 may be a Metal Semiconductor Field Effect Transistor (MESFET) fabricated using GaAs processing. Other transistor configurations are also possible for instance, High Electron Mobility Transistors (HEMT), heterostructure FETs, homogenous or heterojunction bipolar transistors, or PN junctions devices such as PIN diodes to name a few. Other active or passive array elements may be used alternatively or addition to these as well.

In the embodiment of FIG. 7B, the source and drain terminals 712 and 714 of FET 710 are employed as the input and output ports, 711 and 715 respectively and the on/off state of the FET 710 is controlled via a voltage applied to the gate terminal 714. The sample is applied over FET 710 such that the MBR 716 provides a parallel path between the source and drain terminals 712 and 714. FET 710 is designed such that when turned off, it presents a drain to source resistance ($R_{ds}$) which is much higher than resistance through the MBR 716. In this instance, the signal path propagates through the MBR 716 which modulates the test signal. The modulated test signal is recovered (through a DC blocking capacitor to remove the DC bias) and compared to the input test signal to detect and/or identify the molecular binding events occurring within the MBR 716. When the FET 710 is activated, it provides a much lower $R_{ds}$ compared to the resistance of the MBR 716. In this instance, the MBR 716 is effectively switched out of the signal path and the signal propagates largely unaffected by it. Thus by simply opening or closing a switch, an array element may be addressed.

Figure 7C:
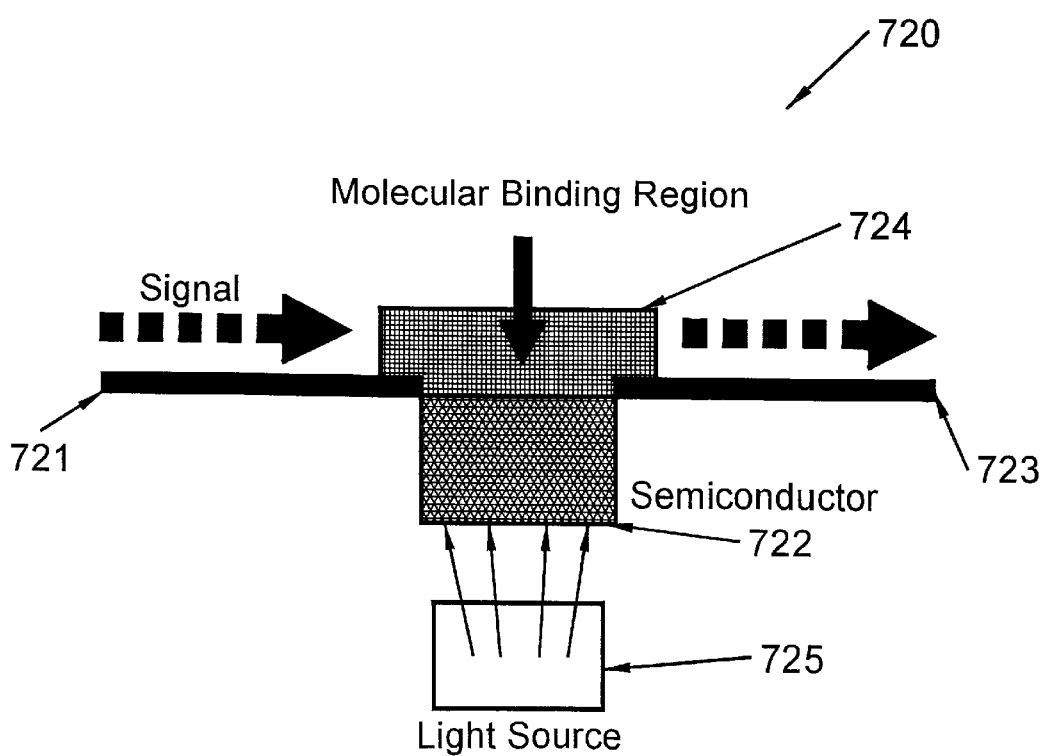
FIG. 7C illustrates one embodiment of an array element in accordance with the present invention comprising a series-connected, optically switched Field Effect Transistor.

FIG. 7C illustrates a further embodiment of a FET used as an array element which is optically switched. FET 720 is connected similarly to FET 710 described in FIG. 7B and may consist of a photosensitive transistor, diode or other photosensitive device. The gate junction 722 may be illuminated, for instance, with normal sunlight, a laser, a Light Emitting Diode (LED), or other source having a wavelength to which FET 720 has a high sensitivity. The incident light activates FET 720 to switch out the MBR 722. When the FET 720 is deactivated, the test signal propagates from FET 721 to FET output 723 through the MBR 722 and is modulated thereby. The modulated test signal is recovered (through a DC blocking capacitor not shown) and analyzed to determine the presence and/or identity of molecular binding events within the MBR 722.

Figure 7D:
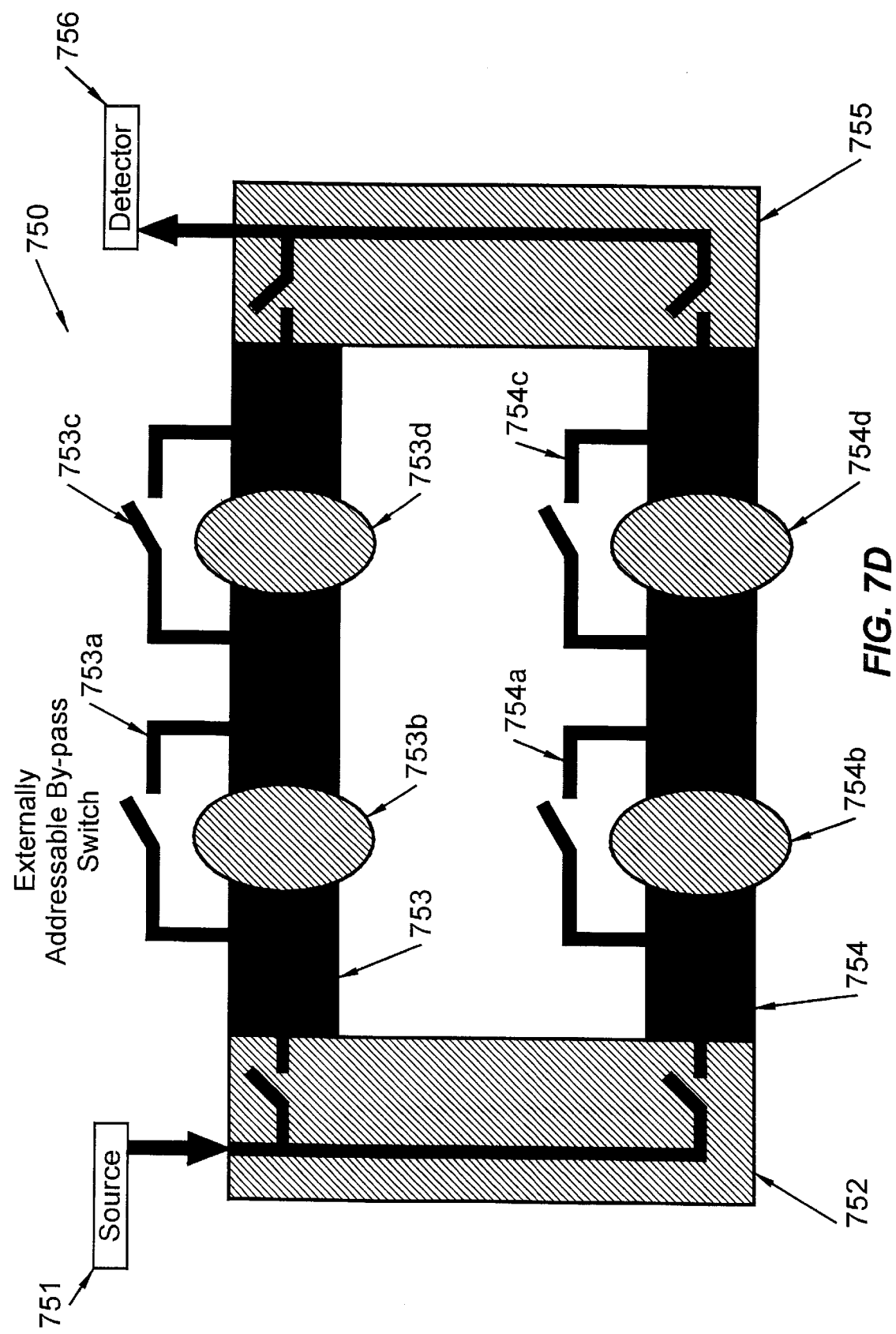
FIG. 7D illustrates one embodiment of an array in accordance with the present invention comprising two paths of two, serially-connected FET devices.

FIG. 7D illustrates an extension of FIGS. 7B and 7C in which two or more FETs are serially-connected. Array 750 includes a first test path 753 along which addressable switches 753a and 753c are coupled. In one embodiment, addressable switches are electronically or optically controlled MESFETs, described above. Array path 753 further includes sample regions 753b and 753d, each of which provides a parallel signal paths to the corresponding addressable switches 753a and 753c.

As described above, addressable switches 753a and 753c operate to switch in and out the sample regions 753b and 753d between a signal source 751 and a signal detector 756 via input switch 752 and output switch 755. Thus, a particular row is made into a transmission path in which a single assay site appears as an impedance mismatch. Each assay site can be either switched into the circuit, or switched out of the circuit, as desired. The nature of the impedance mismatch is a function of binding and other changes in the MBR. Additional signal paths such as signal path 754 (having addressable switches 754a and 754c connected in parallel to sample regions 754b and 754d) may be included in the array and cross-strapped to the other paths using other low loss switches (not shown) to allow the test signal to propagate between signal paths 753 and 754. Input and output switches 752 and 755 are used to inject and recover the test signal to/from the array 750. As those of skill in the art will appreciate, the described array may be extended to any number of N×M elements to provide a two dimensional array device.

Figure 7E:
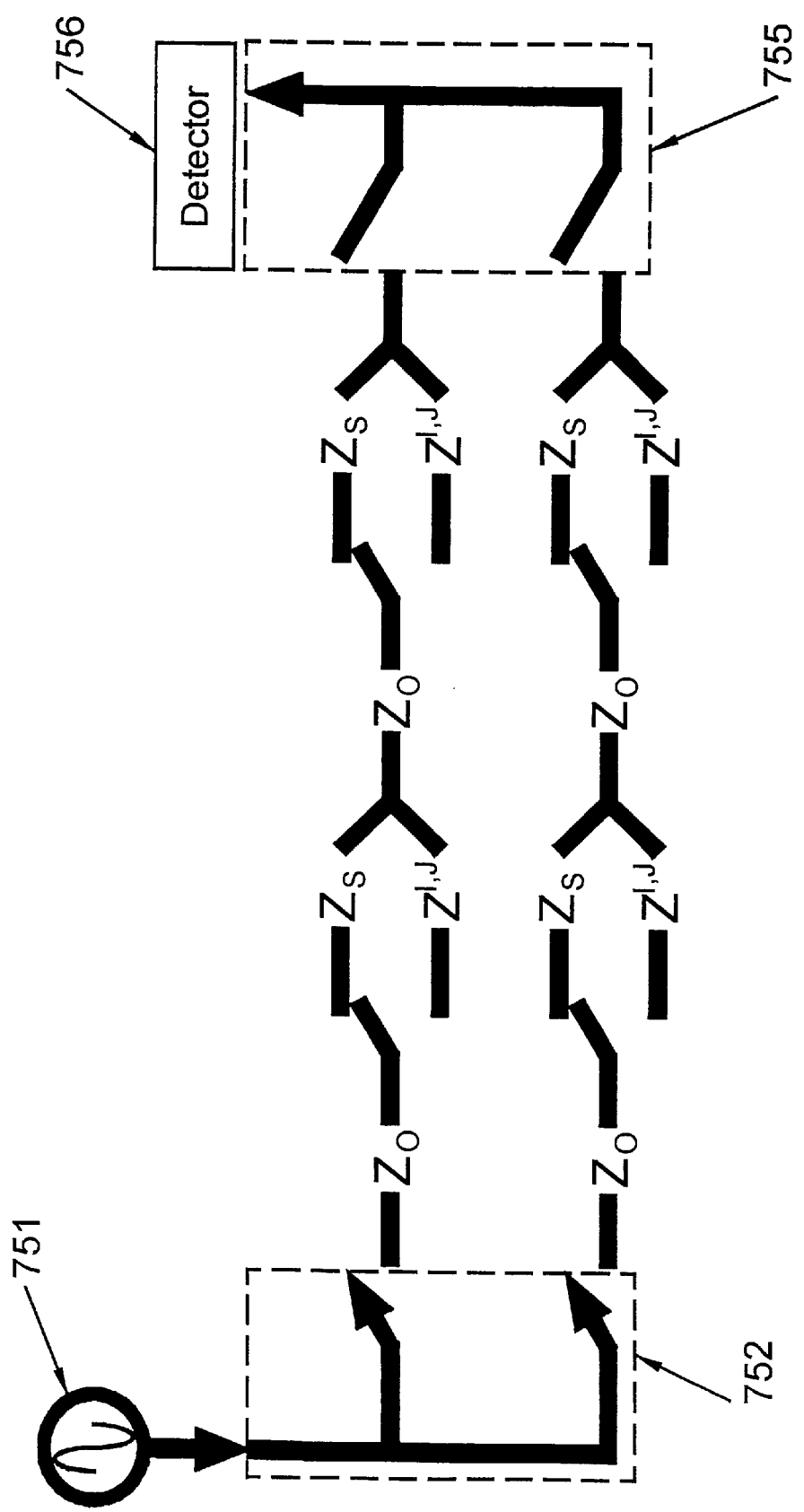
FIG. 7E illustrates the circuit equivalent model of the array shown in FIG. 7D in accordance with the present invention.

FIG. 7E illustrates the circuit equivalent model of the array shown in FIG. 7D. The input source 751, input switch 752, output switch 755, and signal detector 756 are as illustrated in FIG. 7E. The switch impedance Zs is designed to be a close match with the reference impedance of the signal path Zo, and the assay impedance $Z^{ij}$ is designed to be much different than either the switch or reference impedance. Thus, small changes in the assay impedance will dominate the electrical properties of any given row, and will therefore be easily detectable. The exact values for the impedances will depend on the design criteria for the particular array, but certain general principles of engineering apply, such as the greatest efficiency in terms of delivering power to the load (detector) is obtained with matched-impedance design, and reference impedances are frequently taken to be 50 Ω.

In an alternative embodiment, each array element may consist of a logic gate which is capable of occupying one of two possible states, depending on the conditions of gating. As an example, the conditions of gating may be whether or not a particular binding event has occurred. Such a condition may be the hybridization of nucleic acid material to specific capture probes on the surface of the device, or a particular drug-receptor interaction. In any case, the device is engineered so that a binding event or structural change in the MBR triggers the gating. Essentially the modulation of any circuit parameter may trigger the gating; all that is required is to have the necessary hardware and software in place to make the decision as to whether or not the circuit parameter has been modulated.

As an example, one may monitor a characteristic frequency of a given system such as a resonant structure. The shift in this frequency as a result of a particular binding event may serve as the modulation which signals the logic state. Any parameter which changes as a function of binding may be used to trigger logic gate. Such parameters include, but are not limited to: frequency, voltage, current, power, phase, delay, impedance, reactance, admittance, conductance, resistance, capacitance, inductance, or other parameters.

Figure 7F:
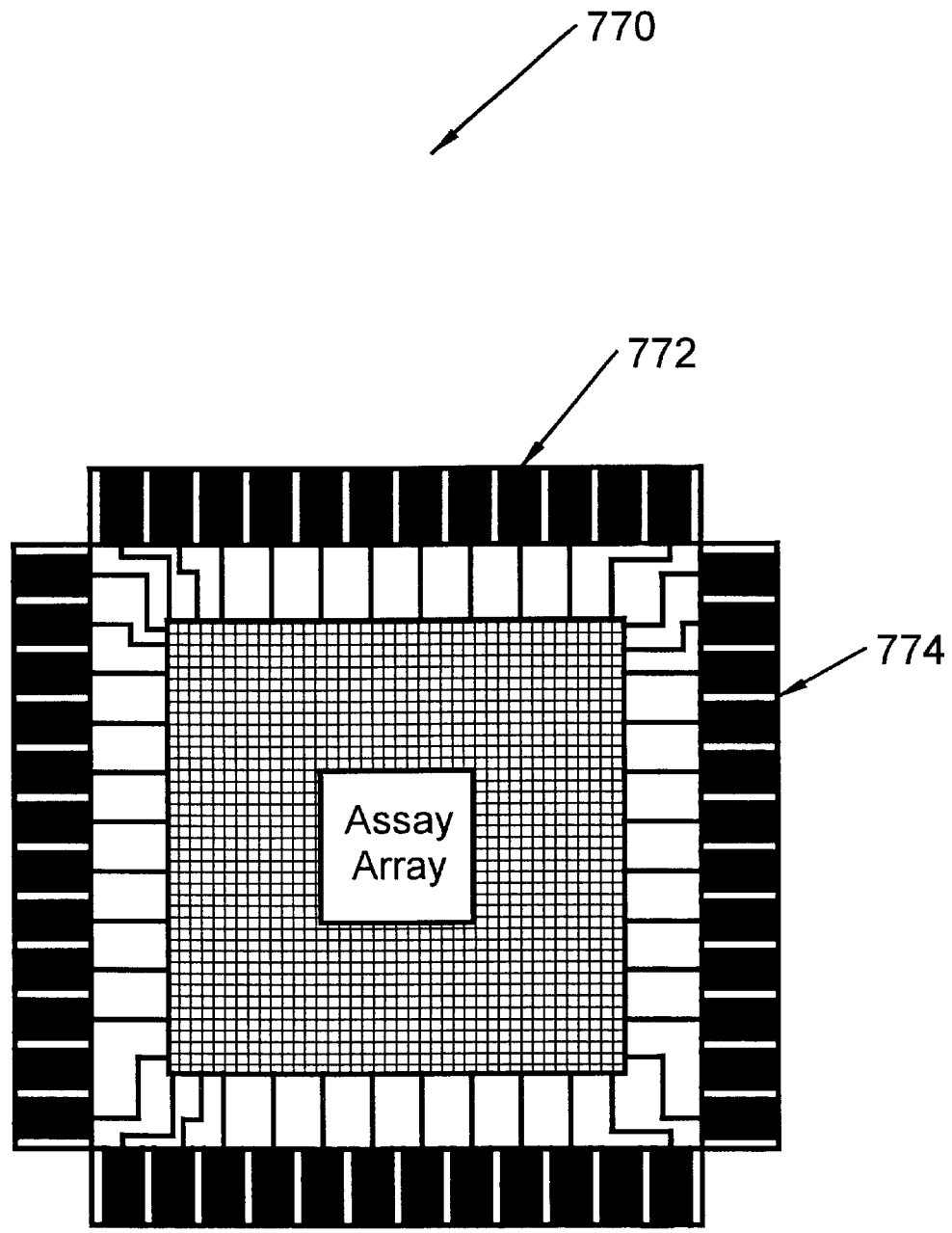
FIG. 7F illustrates one embodiment of a two-dimensional bio-assay array in accordance with the present invention.

FIG. 7F illustrates one embodiment of a two-dimensional bio-assay array 770. As shown, the array 770 includes a first input/output (I/O) axis 772 and a second I/O axis 774 for inputting/outputting test signals.

The array is interfaced with conventional external diagnostic hardware which is capable of generating and detecting the appropriate frequency or frequencies, then communicating it to and from the assay array via a multiplexer, through the ports as illustrated above. Such an externally supported system may be comprised of any number of electromagnetic sources such as vector and scalar network analyzers, time-domain devices like TDR analyzers and other pulsed techniques; utilize any of the detection schemes mentioned herein, including vector and network analyzers; and use any number of well-known techniques to deliver the signals to and from the assay array via standard and non-standard multiplexing techniques.

Generically, such a chip may be fabricated using standard semiconductor chip approaches. Those of skill in the art will readily appreciate that such a configuration may be used in a one-port format, a two port format, or utilize more than two ports.

V. Applications

The above described bio-assay, test fixture, and test system may be used in a number of applications to detect and/or identify particular molecular binding events occurring within the sample. A few of the possible applications are described in general below.

Nucleic Acid Chemistry Application

The bio-sensors and test systems of the present application may be used to analyze binding complexes, such as the hybridization complexes formed between a nucleic acid probe and a nucleic acid target. For instance, the bio-assay sensors and test system may be used in diagnostic methods which involve detecting the presence of one or more target nucleic acids in a sample, quantitative methods, kinetic methods, and a variety of other types of analysis such as sequence checking, expression analysis and de novo sequencing. One or more of these methods may also detect binding between nucleic acids without the use of labels. Certain methods will benefit from utilizing the described bio-assay arrays and test systems which allows for high throughput. Other methods will benefit from the use of spectral profiles which makes it possible to distinguish between different types of hybridization complexes. These methods are further described in the incorporated, concurrently filed patent application entitled "Methods of Nucleic Acid Analysis," Ser. No. 09/365,581.

Drug Discovery Application

The bio-sensors and test systems of the present application may be used to detect binding events between proteins and a variety of different types of ligands. The bio-assay sensors and test systems of the present invention may be used to screen libraries of ligands to identify those ligands which bind to a protein of interest, such methods have particular utility in drug screening programs, for example. Additionally, the bio-assay sensors and test system may be similarly employed with diagnostic methods to detect the presence of a particular ligand that binds to a known protein, or of a particular protein that binds to a known ligand. These methods are further described in the incorporated, concurrently filed patent application entitled "Methods for Analyzing Protein Binding Events," Ser. No. 09/365,580.

Figure 8:
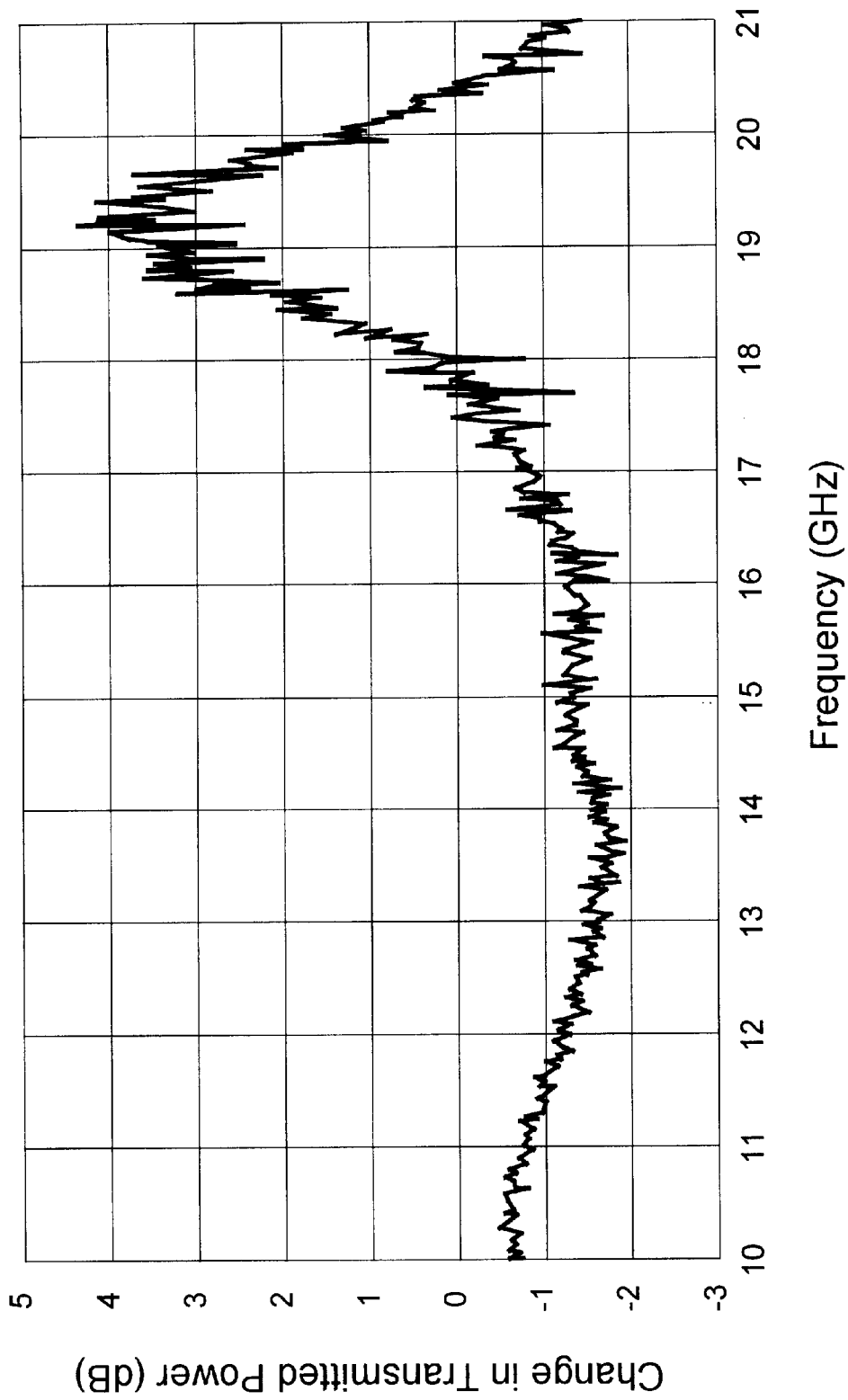
FIG. 8 is an example of the effects of a protein binding non-specifically to the dielectric signal path of the bio-assay device illustrated in FIG. 4E.

FIG. 8 is an example of the effects of a protein binding non-specifically to the dielectric signal path of the bio-assay device 450 illustrated in FIG. 4E. A buffer (d-PBS) was initially placed in the dielectric gap region 455 (FIG. 4E) and a baseline insertion loss measurement over the frequency range 45 MHz to 40 GHz was taken. Next, a sample solution containing urease at high concentration was added and the urease was allowed to bind to the quartz in the dielectric gap region 455. The dielectric region 455 was then flushed with d-PBS and a second insertion loss measurement over the same frequency range was taken. The second measurement was compared to the first resulting in the changes in the signal's frequency response, shown in FIG. 8.

While the above is a complete description of possible embodiments of the invention, various alternatives, modification and equivalents may be used to which the invention is equally applicable. Therefore, the above description should be viewed as only a few possible embodiments of the present invention, the boundaries of which is appropriately defined by the metes and bounds of the following claims.

What is claimed is:

1. A bio-assay array test system, comprising:
    (1) a test fixture comprising:
        (a) a bio-assay device comprising a plurality of multiple-port signal paths, each multiple-port signal path having at least one signal input port and one signal output port, the multiple-port signal path operable to support the propagation of a test signal at one or more frequencies from 10 MHz to 1000 GHz and comprising:
            (i) a transmission line connected between the at least one signal input port and the at least one signal output port;
            (ii) a ground element; and
            (iii) a dielectric substrate attached between the transmission line and ground element; and
        (b) a plurality of sample cavities, each of said sample cavities configured to retain a volume of sample adjacent to at least one of said plurality of multiple-port signal paths, whereby an input test signal propagating along the at least one multiple-port signal path is electromagnetically coupled to the adjacently located sample;
    (2) a measurement system having an output connected to the at least one signal input port of the multiple-port signal path and an input connected to the at least one signal output port of the multiple-port signal path, the measurement system configured to transmit, at one or more predefined frequencies, the input test signals to one or more of the plurality of multiple-port signal paths and to receive a modulated test signals from one or more of the plurality of multiple-port signal paths; and
    (3) a computer connected to the measurement system and configured to control the measurement system's transmission of the input test signal and reception of the modulated test signal.

2. The bio-assay array test system of claim 1, wherein the at least a portion of the signal path comprises a coplanar waveguide transmission line structure.

3. The bio-assay array test system of claim 1, wherein the at least a portion of the signal path comprises a microstrip transmission line structure.

4. The bio-assay array test system of claim 1, wherein the at least a portion of the signal path comprises a coaxial transmission line structure.

5. The bio-assay array test system of claim 1, wherein the at least a portion of the signal path comprises a slotline structure.

6. The bio-assay array test system of claim 1, wherein the molecular binding region comprises a drug receptor.

7. The bio-assay array test system of claim 1, wherein the molecular binding region comprises one or more cells.

* * * * *